US011779636B2

(12) United States Patent
Sagi et al.

(10) Patent No.: US 11,779,636 B2
(45) Date of Patent: *Oct. 10, 2023

(54) COMPOSITIONS FOR REMODELING EXTRACELLULAR MATRIX AND METHODS OF USE THEREOF

(71) Applicant: NanoCell Ltd., Rehovot (IL)

(72) Inventors: Irit Sagi, Rehovot (IL); Inna Solomonov, Rishon LeZion (IL); Eldar Zehorai, Tel-Aviv (IL)

(73) Assignee: NanoCell Ltd., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/859,005

(22) Filed: Jul. 7, 2022

(65) Prior Publication Data

US 2022/0347274 A1 Nov. 3, 2022

Related U.S. Application Data

(63) Continuation of application No. 16/903,402, filed on Jun. 17, 2020, now Pat. No. 11,382,959, which is a
(Continued)

(51) Int. Cl.
| | | |
|---|---|---|
| *A61K 38/48* | (2006.01) | |
| *A61K 38/46* | (2006.01) | |
| *A61P 15/00* | (2006.01) | |
| *A61B 17/435* | (2006.01) | |
| *A61D 19/04* | (2006.01) | |
| *A61K 9/00* | (2006.01) | |

(52) U.S. Cl.
CPC ........ *A61K 38/4886* (2013.01); *A61B 17/435* (2013.01); *A61D 19/04* (2013.01); *A61K 9/0034* (2013.01); *A61K 38/46* (2013.01);
*A61P 15/00* (2018.01); *C12Y 304/24* (2013.01); *C12Y 304/24007* (2013.01)

(58) Field of Classification Search
CPC ................ A61K 9/0034; C12Y 304/24; C12Y 304/24007; A61D 19/04; A61B 17/435; A61P 15/00
See application file for complete search history.

(56) References Cited

U.S. PATENT DOCUMENTS

| | | | | |
|---|---|---|---|---|
| 5,360,389 | A | 11/1994 | Chenette | |
| 5,632,995 | A * | 5/1997 | Wade | A61K 35/74 |
| | | | | 424/282.1 |

(Continued)

FOREIGN PATENT DOCUMENTS

| | | |
|---|---|---|
| WO | WO 2011/096775 | 8/2011 |
| WO | WO 2016/156990 | 10/2016 |

OTHER PUBLICATIONS

Communication Pursuant to Article 94(3) EPC dated Oct. 4, 2019 From the European Patent Office Re. Application No. 16771466.6. (5 Pages).

(Continued)

*Primary Examiner* — Samuel G Gilbert

(57) ABSTRACT

The present invention relates to a method for increasing the embryo implantation rate in a mammalian uterus, by administering to the uterus of a mammal an effective amount of an extracellular matrix remodeling enzyme, as well as to a product comprising an extracellular remodeling enzyme.

12 Claims, 22 Drawing Sheets

Related U.S. Application Data continuation of application No. 15/563,994, filed as application No. PCT/IB2016/000526 on Apr. 1, 2016, now Pat. No. 10,722,560.

(60) Provisional application No. 62/142,661, filed on Apr. 3, 2015, provisional application No. 62/142,672, filed on Apr. 3, 2015, provisional application No. 62/142,675, filed on Apr. 3, 2015.

(56) References Cited

U.S. PATENT DOCUMENTS

| | | | |
|---|---|---|---|
| 10,722,560 B2* | 7/2020 | Sagi | A61K 38/46 |
| 11,382,959 B2* | 7/2022 | Sagi | C12Y 304/24 |
| 2001/0006630 A1 | 7/2001 | Yacoby Zccvi | |
| 2002/0088019 A1 | 7/2002 | Yacoby Zeevi | |
| 2004/0185575 A1 | 9/2004 | Kim et al. | |
| 2009/0208977 A1* | 8/2009 | Hudson | C07K 16/2866 435/366 |
| 2010/0036193 A1 | 2/2010 | Pizolato | |
| 2015/0051441 A1* | 2/2015 | Gopichandran | A61K 38/2006 600/35 |
| 2015/0079069 A1 | 3/2015 | Rozkov | |
| 2018/0133293 A1 | 5/2018 | Sagi et al. | |
| 2021/0015907 A1 | 1/2021 | Sagi et al. | |

OTHER PUBLICATIONS

Communication Pursuant to Article 94(3) EPC dated May 29, 2020 From the European Patent Office Re. Application No. 16771466.6. (4 Pages).
Examination Report dated Oct. 16, 2020 From the Australian Government, IP Australia Re. Application No. 2016241901. (4 Pages).
International Preliminary Report on Patentability dated Nov. 23, 2017 From the International Bureau of WIPO Re. Application No. PCT/IB2016/000526. (7 Pages).
International Search Report and the Written Opinion dated Aug. 22, 2016 From the International Searching Authority Re. Application No. PCT/IB2016/000526. (7 Pages).
Notice of Allowance dated Mar. 9, 2022 from US Patent and Trademark Office Re. U.S. Appl. No. 16/903,402. (3 pages).
Notice of Allowance dated Mar. 23, 2020 from the US Patent and Trademark Office Re. U.S. Appl. No. 15/563,994. (8 pages).
Office Action dated Jul. 10, 2019 From the Israel Patent Office Re. Application No. 254862 and Its Translation Into English. (6 Pages).
Official Action dated Sep. 14, 2021 From the US Patent and Trademark Office Re. U.S. Appl. No. 16/903,402. (15 Pages).
Official Action dated Sep. 19, 2019 From the US Patent and Trademark Office Re. U.S. Appl. No. 15/563,994. (28 pages).
Patent Examination Report dated Aug. 3, 2021 From the Australian Government, IP Australia Re. Application No. 2016241901. (2 Pages).
Requisition by the Examiner dated Mar. 29, 2022 From the Innovation, Science and Economic Development Canada, Canadian Intellectual Property Office Re. Application No. 2,981,585. (3 pages).
Supplementary European Search Report and the European Search Opinion dated Oct. 24, 2018 From the European Patent Office Re Application No. 16771466.6.
Anacker et al. "Human Decidua and Invasive Trophoblasts Are Rich Sources of Nearly All Human Matrix Metalloproteinases", Molecular Human Reproduction, XP055512528, 17(10): 637-652, Advanced Access Publication May 12, 2011. Abstract, Figs., Tables.
Burrows et al. "Trophoblast Migration During Human Placental Implantation", Human Reproduction Update , 2(4): 307-321,1996.
Das et al. "Estrogen-Induced Expression of Fos-Related Antigen 1 (FRA-1) Regulates Uterine Stromal Differentiation and Remodeling", The Journal of Biological Chemistry, XP055512523, 287(23): 19622-19630, Published Online Apr. 18, 2012. Abstract, Figs.
Du et al. "Cyclosporin A Promotes Crosstalk Between Human Cytotrophoblast and Decidual Stromal Cell Through Up-Regulating CXCL12/CXCR4 interaction", Human Reproduction, 27(7}: 1955-1965, 2012. Abstract, Fig.6.
Giudice "Potential Biochemical Markers of Utering Receptivity", Human Reproduction, XP055512501, 14(Suppl.2): Dec. 3-16, 1999.
Solomonov et al. "Distinct Biological Events Generated by ECM Proteolysis by Two Homologous Collagenases", Proc. Natl. Acad. Sci. USA, PNAS, 113(39): 10884-10889, Sep. 27, 2016.
Staun-Ram et al. "Expression and Importance of Matrix Metalloproteinase 2 and 9 (MMP-2 and -9) in Human Trophoblast Invasion", Reproductive Biology and Endocrinology, XP021009427, 2(1): 59-1-59-13, Published Online Aug. 4, 2004. Abstract, Figs.
Requisition by the Examiner dated Feb. 14, 2023 From the Innovation, Science and Economic Development Canada, Canadian Intellectual Property Office Re. Application No. 2,981,585. (3 Pages).

* cited by examiner

Figure 20

| Cleavage site | MMP1 spectral counts | MMP13 spectral counts |
|---|---|---|
| α1(I) | | |
| G827 | | |
| G905 | | |
| G950 | | |
| G953 | | |
| G971 | | |
| α2(I) | | |
| G223 | | |
| P390 | | |
| G508 | | |
| G649 | | |
| G679 | | |
| L786 | | |
| G817 | | |
| H883 | | |
| G886 | | |
| G892 | | |
| P914 | | |
| H944 | | |
| G946 | | |
| L947 | | |

COMPOSITIONS FOR REMODELING EXTRACELLULAR MATRIX AND METHODS OF USE THEREOF

RELATED APPLICATIONS

This application is a continuation of U.S. patent application Ser. No. 16/903,402 filed on Jun. 17, 2020, which is a continuation of U.S. patent application Ser. No. 15/563,994 filed on Oct. 3, 2017, now U.S. Pat. No. 10,722,560, which is a National Phase of PCT Patent Application No. PCT/IB2016/000526 having International Filing Date of Apr. 1, 2016, which claims the benefit of priority under 35 USC § 119(e) of U.S. Provisional Patent Application No. 62/142,661 filed on Apr. 3, 2015, U.S. Provisional Patent Application No. 62/142,675 filed on Apr. 3, 2015, and U.S. Provisional Patent Application No. 62/142,672 filed on Apr. 3, 2015. The contents of the above applications are all incorporated by reference as if fully set forth herein in their entirety.

FIELD AND BACKGROUND OF THE INVENTION

The present invention relates to a method for increasing the embryo implantation rate in a mammalian uterus, by administering to the uterus of a mammal an effective amount of an extracellular matrix remodeling enzyme, as well as to a product comprising an extracellular remodeling enzyme.

Degradation of extracellular matrix (ECM) is critical for many processes orchestrating tissue homeostasis and pathology.

SUMMARY OF THE INVENTION

In one embodiment, the present invention provides a method, wherein the method increases the rate of embryo implantation in the uterus of a mammal, the method comprising:
 a) administering at least one extra cellular matrix (ECM) remodeling enzyme selected from the group consisting of matrix metalloproteinase (MMP)-1, MMP-2, MMP-3, MMP-7, MMP-8 MMP-9, MMP-10, MMP-11, MMP-12, MMP-13, MMP-14, MMP-15, MMP-16, MMP-17, MMP-19, MMP-20, MMP-21, MMP-23, MMP-24, MMP-25, MMP-26, MMP-27, and MMP-28, to the mammal's uterus; and
 b) introducing at least one embryo into the treated uterus and allowing the introduced embryo to implant into the endometrium of the uterus.

In one embodiment, the present invention provides a method, wherein the method increases the rate of embryo implantation in the uterus of a mammal, the method comprising:
 a) administering at least one extra cellular matrix (ECM) remodeling enzyme selected from the group consisting of matrix metalloproteinase (MMP)-1, MMP-2, MMP-3, MMP-7, MMP-8 MMP-9, MMP-10, MMP-11, MMP-12, MMP-13, MMP-14, MMP-15, MMP-16, MMP-17, MMP-19, MMP-20, MMP-21, MMP-23, MMP-24, MMP-25, MMP-26, MMP-27, and MMP-28, to a uterus of a mammal.

In one embodiment, the at least one extra cellular matrix (ECM) remodeling enzyme is administered to the mammal's uterus at an amount sufficient to remodel the ECM of the endometrium of the uterus.

In one embodiment, the at least one extra cellular matrix (ECM) remodeling enzyme is administered to the mammal's uterus for a time sufficient to remodel the ECM of the endometrium of the uterus.

In one embodiment, the rate of implantation of the at least one embryo is greater in a mammal treated with the ECM remodeling enzyme, compared to the rate of implantation a non-treated mammal.

In one embodiment, the present invention provides a method, wherein the method increases the rate of embryo implantation in the uterus of a mammal, the method comprising:
 a) contacting at least one embryo with at least one ECM remodeling enzyme selected from the group consisting of matrix metalloproteinase (MMP)-1, MMP-2, MMP-3, MMP-7, MMP-8 MMP-9, MMP-10, MMP-11, MMP-12, MMP-13, MMP-14, MMP-15, MMP-16, MMP-17, MMP-19, MMP-20, MMP-21, MMP-23, MMP-24, MMP-25, MMP-26, MMP-27, and MMP-28; and
 b) introducing at least one treated embryo into a treated uterus of a mammal and allowing the introduced embryo to implant.

In one embodiment, the at least one embryo is contacted with the at least one extra cellular matrix (ECM) remodeling enzyme at an amount sufficient to remodel the ECM of the at least one embryo.

In one embodiment, the at least one embryo is contacted with the at least one extra cellular matrix (ECM) remodeling enzyme for a time sufficient to remodel the ECM of the at least one embryo.

In one embodiment, the rate of implantation of the at least one embryo is greater following treatment of the at least one embryo with the ECM remodeling enzyme, compared to the rate of implantation a non-treated at least one embryo.

In one embodiment, the at least one ECM remodeling enzyme further comprises products produced by digesting ECM with the at least one ECM remodeling enzyme.

In one embodiment, amount sufficient to remodel the ECM is from 0.1 to 10000 ng.

In one embodiment, the amount sufficient to remodel the ECM is from 0.5 to 50 μM.

In one embodiment, the time sufficient to remodel the ECM is from 10 minutes to 72 hours.

BRIEF DESCRIPTION OF THE SEVERAL VIEWS OF THE DRAWINGS

In the drawings:

FIG. 1A shows micrographs of murine oocytes adhered to ECM fascicles treated according to some embodiments of the present invention (MMP1), and murine oocytes adhered to untreated ECM fascicles (control). FIG. 1B shows the average number of murine oocytes adhered per collagen fibril, for untreated collagen fibrils (uncut) and collagen fibrils treated according to some embodiments of the present invention (MMP1).

FIG. 2A shows micrographs of murine embryos adhered to ECM fascicles treated according to some embodiments of the present invention (MMP1), and murine oocytes adhered to untreated collagen fibrils (control). FIG. 2B shows the average number of murine embryos adhered per collagen fibril, for untreated collagen fibrils (uncut) and collagen fibrils treated according to some embodiments of the present invention (MMP1).

FIG. 4A shows the fold increase in the number of embryos implanted in uteri treated with MMP-1 (MMP1), compared to control animals (control). (n=20 for each group, p value less than 0.01). FIG. 4B shows micrographs of embryos implanted in a murine uterus treated with MMP-1 according to some embodiments of the present invention (MMP1), and an untreated murine uterus (control). The positions of the implanted embryos are indicated by arrows.

FIG. 5A shows the fold increase in the number of endogenous embryos implanted in uteri treated with MMP-1 (MMP1), compared to control animals (control) under normal conditions (Endogenous), or heat stress conditions (Heat Stress). n=10 per treatment group. FIG. 5B shows micrographs of endogenous embryos implanted in a murine uterus treated with MMP-1 according to some embodiments of the present invention, under heat stress (heat stress), and a murine uterus treated with MMP-1 according to some embodiments of the present invention, under normal conditions (endogenous). The positions of the implanted embryos are indicated by mows.

FIG. 6A shows Rat-1 fibroblasts were seeded and grown for 24 and 72 h. Collagen production and deposition was not detected using 2-photon microscopy in a Second Harmonics Generation (SHG) mode, as compared to the positive control. FIG. 6B shows Western blot analysis produced from lysates and media of rat-1 cells, demonstrate minimal secretion of MMP-1 and MMP-13 upon 24 h. Rat-1 cells were grown up to 24 h. 4 and 24 h post deeding, medium was collected and cell were lysed, and analyzed using western blot for detection of MMP1 and MMP13. As a positive control, 50 ng/mL of recombinant protein (either MMP1 or MMP13) were loaded. Quantification of protein secretion was performed using ImageJ and detected approximately 0.5 ng/mL of MMP-1 in cell lysates and 5 ng/mL of MMP-13 in the medium.

FIG. 20 shows the sporadic cleavage sites produced by the degradation of Col by MMP-1 and MMP-13. Lighter shading: common sites. Darker shading: individual cleavage sites. The absolute number of spectralcounts identified for each semi-tryptic peptide from silver stained SDS-PAGE is shown.

FIG. 22A shows a micrograph of rat-1 cells interacting with intact Col I ECM. FIG. 22B shows a micrograph of Rat-1 cells interacting with Col I ECM treated with MMP-1 according to some embodiments of the present invention.

DESCRIPTION OF SPECIFIC EMBODIMENTS OF THE INVENTION

Figure 1A:
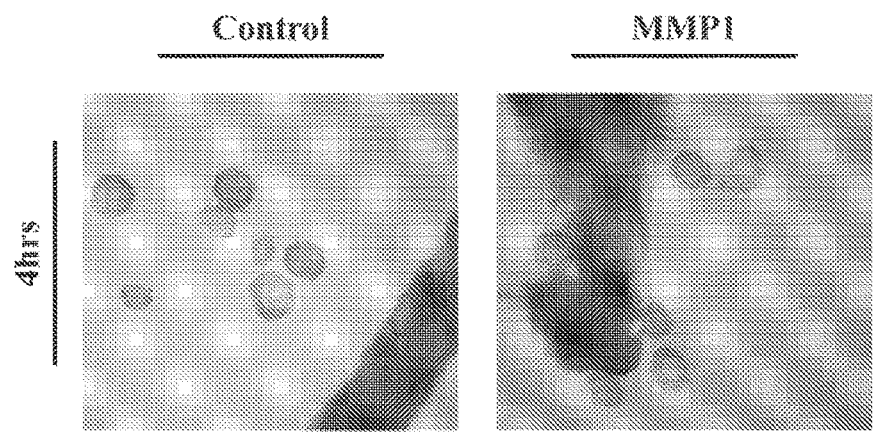
FIGS. 1A-1B.

For clarity of disclosure, and not by way of limitation, the detailed description of the invention is divided into the following subsections that describe or illustrate certain features, embodiments or applications of the present invention.

As used herein, "implantation rate", or "rate of implantation" refers to the number of embryos that adhere to the endometrium of mammals after, whether or not generated by assisted reproduction technology.

Without intending to be limited to any particular theory, a successful human pregnancy via in vitro fertilization ("IVF") is dependent on several factors, such as, for example, follicular development, number of oocytes retrieved fertilization, embryo development and implantation. Implantation of the embryo is a complex process, dependent on factors such as, for example, structural changes in the endometrium and the developing embryo.

Without intending to be limited to any particular theory, tissue remodeling, such as, for example, remodeling of the extra cellular matrix ("ECM") is requisite to uterine preparation, embryonic breaching of the epithelial basement membrane and subsequent penetration of the endometrial stroma.

In some embodiments, the present invention provides a method, wherein the method increases the rate of embryo implantation in the uterus of a mammal, the method comprising:
a) administering at least one extra cellular matrix (ECM) remodeling enzyme selected from the group consisting of matrix metalloproteinase (MMP)-1, MMP-2, MMP-3, MMP-7, MMP-8 MMP-9, MMP-10, MMP-11, MMP-12, MMP-13, MMP-14, MMP-15, MMP-16, MMP-17, MMP-19, MMP-20, MMP-21, MMP-23, MMP-24, MMP-25, MMP-26, MMP-27, and MMP-28, to the mammal's uterus; and
b) introducing at least one embryo into the treated uterus and allowing the introduced embryo to implant into the endometrium of the uterus.

In some embodiments, the at least one extra cellular matrix (ECM) remodeling enzyme is administered to the mammal's uterus at an amount sufficient to remodel the ECM of the endometrium of the uterus.

In some embodiments, the at least one extra cellular matrix (ECM) remodeling enzyme is administered to the mammal's uterus for a time sufficient to remodel the ECM of the endometrium of the uterus.

In some embodiments, the rate of implantation of the at least one embryo is greater in a mammal treated with the ECM remodeling enzyme, compared to the rate of implantation a non-treated mammal.

In some embodiments, the mammal is a human. Alternatively, in some embodiments, the mammal is a cow. Alternatively, in some embodiments, the mammal is a dog. Alternatively, in some embodiments, the mammal is a rodent.

In some embodiments, the at least one embryo is generated in vitro via in vitro fertilization. In some embodiments, the uterus is treated with the at least one ECM remodeling enzyme prior to introducing the at least one embryo into the uterus. Alternatively, in some embodiments, the uterus is treated with the at least one ECM remodeling enzyme concurrently with the introduction of the at least one embryo.

In some embodiments, the mammal is undergoing an assisted reproductive therapy program. In some embodiments, the assisted reproductive therapy program comprises:
  a) prestimulation treatment; followed by
  b) ovarian stimulation with factors such as, for example gonadotrophins; followed by
  c) monitoring follicle development with ultrasound and serum hormone levels; followed by
  d) maturation of the oocyts and hCG administration; followed by
  e) transvaginal oocyte retrieval;
  f) insemination; followed by
  g) embryo transfer.

In some embodiments, prior to the embryo transfer of the assisted reproductive therapy program, the mammal is treated by:
  a) administering at least one extra cellular matrix (ECM) remodeling enzyme selected from the group consisting of matrix metalloproteinase (MMP)-1, MMP-2, MMP-3, MMP-7, MMP-8 MMP-9, MMP-10, MMP-11, MMP-12, MMP-13, MMP-14, MMP-15, MMP-16, MMP-17, MMP-19, MMP-20, MMP-21, MMP-23, MMP-24, MMP-25, MMP-26, MMP-27, and MMP-28, to the mammal's uterus; and
  b) introducing at least one embryo into the treated uterus and allowing the introduced embryo to implant into the endometrium of the uterus.

In some embodiments, the at least one extra cellular matrix (ECM) remodeling enzyme is administered to the mammal's uterus at an amount sufficient to remodel the ECM of the endometrium of the uterus.

In some embodiments, the at least one extra cellular matrix (ECM) remodeling enzyme is administered to the mammal's uterus for a time sufficient to remodel the ECM of the endometrium of the uterus.

In some embodiments, the rate of implantation of the at least one embryo is greater in a mammal treated with the ECM remodeling enzyme, compared to the rate of implantation a non-treated mammal.

In some embodiments, pseudopregnancy has been induced in the mammal. In some embodiments, the mammal is treated 1 day post copulation. Alternatively, the mammal is treated 2 days post copulation. Alternatively, the mammal is treated 2.5 days post copulation. Alternatively, the mammal is treated 3 days post copulation. Alternatively, the mammal is treated 3.5 days post copulation. Alternatively, the mammal is treated 4 days post copulation.

In some embodiments, the uterus is treated with the at least one ECM remodeling enzyme for 12 hours. Alternatively, the uterus is treated with the at least one ECM remodeling enzyme for 10 hours. Alternatively, the uterus is treated with the at least one ECM remodeling enzyme for 9 hours. Alternatively, the uterus is treated with the at least one ECM remodeling enzyme for 8 hours. Alternatively, the uterus is treated with the at least one ECM remodeling enzyme for 7 hours. Alternatively, the uterus is treated with the at least one ECM remodeling enzyme for 6 hours. Alternatively, the uterus is treated with the at least one ECM remodeling enzyme for 5 hours. Alternatively, the uterus is treated with the at least one ECM remodeling enzyme for 4 hours. Alternatively, the uterus is treated with the at least one ECM remodeling enzyme for 3 hours. Alternatively, the uterus is treated with the at least one ECM remodeling enzyme for 2 hours. Alternatively, the uterus is treated with the at least one ECM remodeling enzyme for 1 hour. Alternatively, the uterus is treated with the at least one ECM remodeling enzyme for 30 minutes. Alternatively, the uterus is treated with the at least one ECM remodeling enzyme for 20 minutes. Alternatively, the uterus is treated with the at least one ECM remodeling enzyme for 10 minutes Alternatively, the uterus is treated with the at least one ECM remodeling enzyme for 9 minutes Alternatively, the uterus is treated with the at least one ECM remodeling enzyme for 8 minutes Alternatively, the uterus is treated with the at least one ECM remodeling enzyme for 7 minutes Alternatively, the uterus is treated with the at least one ECM remodeling enzyme for 6 minutes Alternatively, the uterus is treated with the at least one ECM remodeling enzyme for 5 minutes Alternatively, the uterus is treated with the at least one ECM remodeling enzyme for 4 minutes Alternatively, the uterus is treated with the at least one ECM remodeling enzyme for 3 minutes Alternatively, the uterus is treated with the at least one ECM remodeling enzyme for 2 minutes Alternatively, the uterus is treated with the at least one ECM remodeling enzyme for 1 minute.

In some embodiments, the amount of the at least one ECM remodeling enzyme that is sufficient to remodel the ECM is affected by factors, such as, but not limited to, the species of the mammal, the number of embryos implanted, the size of the uterus to be treated, the surface area of the uterus to be treated, the volume of the uterus to be treated, the age of the mammal the size of the mammal, the weight of the mammal, the particular ECM remodeling enzyme chosen, and the like.

In some embodiments, between 0.1 to 10000 ng of the at least one ECM remodeling enzyme is administered to the uterus of a mammal. In some embodiments, between 0.1 to 1000 ng of the at least one ECM remodeling enzyme is administered to the uterus of a mammal. In some embodiments, between 0.1 to 100 ng of the at least one ECM remodeling enzyme is administered to the uterus of a mammal. In some embodiments, between 0.1 to 80 ng of the at least one ECM remodeling enzyme is administered to the uterus of a mammal. In some embodiments, between 0.1 to 60 ng of the at least one ECM remodeling enzyme is administered to the uterus of a mammal. In some embodiments, between 0.1 to 40 ng of the at least one ECM remodeling enzyme is administered to the uterus of a mammal. In some embodiments, between 0.1 to 20 ng of the at least one ECM remodeling enzyme is administered to the uterus of a mammal. In some embodiments, between 0.1 to 15 ng of the at least one ECM remodeling enzyme is administered to the uterus of a mammal of an embryo. In some embodiments, between 0.1 to 10 ng of the at least one ECM remodeling enzyme is administered to the uterus of a mammal. In some embodiments, between 0.1 to 5 ng of the at least one ECM remodeling enzyme is administered to the uterus of a mammal. In some embodiments, between 0.1 to 1 ng of the at least one ECM remodeling enzyme is administered to the uterus of a mammal.

In some embodiments, between 0.5 µM to 50 µM of the at least one ECM remodeling enzyme is administered to the uterus of a mammal. In some embodiments, 0.5 µM of the at least one ECM remodeling enzyme is administered to the uterus of a mammal. In some embodiments, 0.5 µM of the at least one ECM remodeling enzyme is administered to the uterus of a mammal. In some embodiments, 0.5 µM of the at least one ECM remodeling enzyme is administered to the uterus of a mammal. In some embodiments, 1 µM of the at least one ECM remodeling enzyme is administered to the uterus of a mammal. In some embodiments, 2 µM of the at least one ECM remodeling enzyme is administered to the uterus of a mammal. In some embodiments, 3 µM of the at least one ECM remodeling enzyme is administered to the uterus of a mammal. In some embodiments, 4 µM of the at least one ECM remodeling enzyme is administered to the uterus of a mammal. In some embodiments, 5 µM of the at least one ECM remodeling enzyme is administered to the uterus of a mammal. In some embodiments, 6 µM of the at least one ECM remodeling enzyme is administered to the uterus of a mammal. In some embodiments, 7 µM of the at least one ECM remodeling enzyme is administered to the uterus of a mammal. In some embodiments, 8 µM of the at least one ECM remodeling enzyme is administered to the uterus of a mammal. In some embodiments, 9 µM of the at least one ECM remodeling enzyme is administered to the uterus of a mammal. In some embodiments, 10 µM of the at least one ECM remodeling enzyme is administered to the uterus of a mammal. In some embodiments, 20 µM of the at least one ECM remodeling enzyme is administered to the uterus of a mammal. In some embodiments, 30 µM of the at least one ECM remodeling enzyme is administered to the uterus of a mammal. In some embodiments, 40 µM of the at least one ECM remodeling enzyme is administered to the uterus of a mammal. In some embodiments, 50 µM of the at least one ECM remodeling enzyme is administered to the uterus of a mammal.

The volume that is administered into the uterus of the mammal is dependent on a number of factors, such as, for example, the species of mammal, the area of the uterus to be treated, the volume of the uterus, and the like. Thus, in some embodiments, the volume is sufficient to deliver the at least one ECM remodeling enzyme in an amount sufficient to remodel the ECM of the endometrium of the uterus. For example, by way of illustration, in the mouse, the volume is from 1 µl to 5 µl.

In some embodiments, between 1 to 20 ng of the at least one ECM remodeling enzyme is administered to the uterus of a mammal. In some embodiments, between 5 to 20 ng of the at least one ECM remodeling enzyme is administered to the uterus of a mammal. In some embodiments, between 10 to 20 ng of the at least one ECM remodeling enzyme is administered to the uterus of a mammal. In some embodiments, between 15 to 20 ng of the at least one ECM remodeling enzyme is administered to the uterus of a mammal. In some embodiments, between 5 to 15 ng of the at least one ECM remodeling enzyme is administered to the uterus of a mammal.

In some embodiments, 100% of the endometrium of the uterus is treated. In some embodiments, less than 100% of the endometrium of the uterus is treated. In some embodiments, 90% of the endometrium of the uterus is treated. In some embodiments, 80% of the endometrium of the uterus is treated. In some embodiments, 70% of the endometrium of the uterus is treated. In some embodiments, 60% of the endometrium of the uterus is treated. In some embodiments, 50% of the endometrium of the uterus is treated. In some embodiments, 40% of the endometrium of the uterus is treated. In some embodiments, 30% of the endometrium of the uterus is treated. In some embodiments, 20% of the endometrium of the uterus is treated. In some embodiments, 10% of the endometrium of the uterus is treated. In some embodiments, 9% of the endometrium of the uterus is treated. In some embodiments, 8% of the endometrium of the uterus is treated. In some embodiments, 7% of the endometrium of the uterus is treated. In some embodiments, 6% of the endometrium of the uterus is treated. In some embodiments, 5% of the endometrium of the uterus is treated. In some embodiments, 4% of the endometrium of the uterus is treated. In some embodiments, 3% of the endometrium of the uterus is treated. In some embodiments, 2% of the endometrium of the uterus is treated. In some embodiments, 1% of the endometrium of the uterus is treated.

In some embodiments, treatment of a uterus with the at least one ECM remodeling enzyme results in between a 10% to 50% increase in the rate of implantation of an embryo, compared to a non-treated uterus. In some embodiments, treatment of a uterus with the at least one ECM remodeling enzyme results in between a 15% to 50% increase in the rate of implantation of an embryo, compared to a non-treated uterus. In some embodiments, treatment of a uterus with the at least one ECM remodeling enzyme results in between a 20% to 50% increase in the rate of implantation of an embryo, compared to a non-treated uterus. In some embodiments, treatment of a uterus with the at least one ECM remodeling enzyme results in between a 25% to 50% increase in the rate of implantation of an embryo, compared to a non-treated uterus. In some embodiments, treatment of a uterus with the at least one ECM remodeling enzyme results in between a 30% to 50% increase in the rate of implantation of an embryo, compared to a non-treated uterus. In some embodiments, treatment of a uterus with the at least one ECM remodeling enzyme results in between a 35% to 50% increase in the rate of implantation of an embryo, compared to a non-treated uterus. In some embodiments, treatment of a uterus with the at least one ECM remodeling enzyme results in between a 40% to 50% increase in the rate of implantation of an embryo, compared to a non-treated uterus. In some embodiments, treatment of a uterus with the at least one ECM remodeling enzyme results in between a 45% to 50% increase in the rate of implantation of an embryo, compared to a non-treated uterus.

In some embodiments, treatment of a uterus with the at least one ECM remodeling enzyme results in a 4 fold increase in the rate of adhesion the at least one embryo to the ECM of the endometrium of the uterus, compared to a non-treated uterus. In some embodiments, treatment of a uterus with the at least one ECM remodeling enzyme results in a 3.9 fold increase in the rate of adhesion the at least one embryo to the ECM of the endometrium of the uterus, compared to a non-treated uterus. In some embodiments, treatment of a uterus with the at least one ECM remodeling enzyme results in a 3.8 fold increase in the rate of adhesion the at least one embryo to the ECM of the endometrium of the uterus, compared to a non-treated uterus. In some embodiments, treatment of a uterus with the at least one ECM remodeling enzyme results in a 3.7 fold increase in the rate of adhesion the at least one embryo to the ECM of the endometrium of the uterus, compared to a non-treated uterus. In some embodiments, treatment of a uterus with the at least one ECM remodeling enzyme results in a 3.6 fold increase in the rate of adhesion the at least one embryo to the ECM of the endometrium of the uterus, compared to a non-treated uterus. In some embodiments, treatment of a uterus with the at least one ECM remodeling enzyme results in a 3.5 fold increase in the rate of adhesion the at least one embryo to the ECM of the endometrium of the uterus, compared to a non-treated uterus. In some embodiments, treatment of a uterus with the at least one ECM remodeling enzyme results in a 3.4 fold increase in the rate of adhesion the at least one embryo to the ECM of the endometrium of the uterus, compared to a non-treated uterus. In some embodiments, treatment of a uterus with the at least one ECM remodeling enzyme results in a 3.3 fold increase in the rate of adhesion the at least one embryo to the ECM of the endometrium of the uterus, compared to a non-treated uterus. In some embodiments, treatment of a uterus with the at least one ECM remodeling enzyme results in a 3.2 fold increase in the rate of adhesion the at least one embryo to the ECM of the endometrium of the uterus, compared to a non-treated uterus. In some embodiments, treatment of a uterus with the at least one ECM remodeling enzyme results in a 3.1 fold increase in the rate of adhesion the at least one embryo to the ECM of the endometrium of the uterus, compared to a non-treated uterus. In some embodiments, treatment of a uterus with the at least one ECM remodeling enzyme results in a 3 fold increase in the rate of adhesion the at least one embryo to the ECM of the endometrium of the uterus, compared to a non-treated uterus. In some embodiments, treatment of a uterus with the at least one ECM remodeling enzyme results in a 2.9 fold increase in the rate of adhesion the at least one embryo to the ECM of the endometrium of the uterus, compared to a non-treated uterus. In some embodiments, treatment of a uterus with the at least one ECM remodeling enzyme results in a 2.8 fold increase in the rate of adhesion the at least one embryo to the ECM of the endometrium of the uterus, compared to a non-treated uterus. In some embodiments, treatment of a uterus with the at least one ECM remodeling enzyme results in a 2.7 fold increase in the rate of adhesion the at least one embryo to the ECM of the endometrium of the uterus, compared to a non-treated uterus. In some embodiments, treatment of a uterus with the at least one ECM remodeling enzyme results in a 2.6 fold increase in the rate of adhesion the at least one embryo to the ECM of the endometrium of the uterus, compared to a non-treated uterus. In some embodiments, treatment of a uterus with the at least one ECM remodeling enzyme results in a 2.5 fold increase in the rate of adhesion the at least one embryo to the ECM of the endometrium of the uterus, compared to a non-treated uterus. In some embodiments, treatment of a uterus with the at least one ECM remodeling enzyme results in a 2.4 fold increase in the rate of adhesion the at least one embryo to the ECM of the endometrium of the uterus, compared to a non-treated uterus. In some embodiments, treatment of a uterus with the at least one ECM remodeling enzyme results in a 2.3 fold increase in the rate of adhesion the at least one embryo to the ECM of the endometrium of the uterus, compared to a non-treated uterus. In some embodiments, treatment of a uterus with the at least one ECM remodeling enzyme results in a 2.2 fold increase in the rate of adhesion the at least one embryo to the ECM of the endometrium of the uterus, compared to a non-treated uterus. In some embodiments, treatment of a uterus with the at least one ECM remodeling enzyme results in a 2.1 fold increase in the rate of adhesion the at least one embryo to the ECM of the endometrium of the uterus, compared to a non-treated uterus. In some embodiments, treatment of a uterus with the at least one ECM remodeling enzyme results in a 2 fold increase in the rate of adhesion the at least one embryo to the ECM of the endometrium of the uterus, compared to a non-treated uterus. In some embodiments, treatment of a uterus with the at least one ECM remodeling enzyme results in a 1.9 fold increase in the rate of adhesion the at least one embryo to the ECM of the endometrium of the uterus, compared to a non-treated uterus. In some embodiments, treatment of a uterus with the at least one ECM remodeling enzyme results in a 1.8 fold increase in the rate of adhesion the at least one embryo to the ECM of the endometrium of the uterus, compared to a non-treated uterus. In some embodiments, treatment of a uterus with the at least one ECM remodeling enzyme results in a 1.7 fold increase in the rate of adhesion the at least one embryo to the ECM of the endometrium of the uterus, compared to a non-treated uterus. In some embodiments, treatment of a uterus with the at least one ECM remodeling enzyme results in a 1.6 fold increase in the rate of adhesion the at least one embryo to the ECM of the endometrium of the uterus, compared to a non-treated uterus. In some embodiments, treatment of a uterus with the at least one ECM remodeling enzyme results in a 1.5 fold increase in the rate of adhesion the at least one embryo to the ECM of the endometrium of the uterus, compared to a non-treated uterus. In some embodiments, treatment of a uterus with the at least one ECM remodeling enzyme results in a 1.4 fold increase in the rate of adhesion the at least one embryo to the ECM of the endometrium of the uterus, compared to a non-treated uterus. In some embodiments, treatment of a uterus with the at least one ECM remodeling enzyme results in a 1.3 fold increase in the rate of adhesion the at least one embryo to the ECM of the endometrium of the uterus, compared to a non-treated uterus. In some embodiments, treatment of a uterus with the at least one ECM remodeling enzyme results in a 1.2 fold increase in the rate of adhesion the at least one embryo to the ECM of the endometrium of the uterus, compared to a non-treated uterus. In some embodiments, treatment of a uterus with the at least one ECM remodeling enzyme results in a 1.1 fold increase in the rate of adhesion the at least one embryo to the ECM of the endometrium of the uterus, compared to a non-treated uterus.

In some embodiments, the at least one embryo is generated via natural conception. In these embodiments, the uterus is treated with the at least one ECM remodeling enzyme prior to, or post conception. Accordingly, in some embodiments, the present invention provides a method, comprising:
 a) administering at least one extra cellular matrix (ECM) remodeling enzyme selected from the group consisting of matrix metalloproteinase (MMP)-1, MMP-2, MMP-3, MMP-7, MMP-8 MMP-9, MMP-10, MMP-11, MMP-12, MMP-13, MMP-14, MMP-15, MMP-16, MMP-17, MMP-19, MMP-20, MMP-21, MMP-23, MMP-24, MMP-25, MMP-26, MMP-27, and MMP-28, to a uterus of a mammal.

In some embodiments, the at least one extra cellular matrix (ECM) remodeling enzyme is administered to the mammal's uterus at an amount sufficient to remodel the ECM of the endometrium of the uterus.

In some embodiments, the at least one extra cellular matrix (ECM) remodeling enzyme is administered to the mammal's uterus for a time sufficient to remodel the ECM of the endometrium of the uterus.

In some embodiments, the rate of implantation of the at least one embryo is greater in a mammal treated with the ECM remodeling enzyme, compared to the rate of implantation a non-treated mammal.

In some embodiments, the uterus is treated with the at least one ECM remodeling enzyme for 12 hours. Alternatively, the uterus is treated with the at least one ECM remodeling enzyme for 10 hours. Alternatively, the uterus is treated with the at least one ECM remodeling enzyme for 9 hours. Alternatively, the uterus is treated with the at least one ECM remodeling enzyme for 8 hours. Alternatively, the uterus is treated with the at least one ECM remodeling enzyme for 7 hours. Alternatively, the uterus is treated with the at least one ECM remodeling enzyme for 6 hours. Alternatively, the uterus is treated with the at least one ECM remodeling enzyme for 5 hours. Alternatively, the uterus is treated with the at least one ECM remodeling enzyme for 4 hours. Alternatively, the uterus is treated with the at least one ECM remodeling enzyme for 3 hours. Alternatively, the uterus is treated with the at least one ECM remodeling enzyme for 2 hours. Alternatively, the uterus is treated with the at least one ECM remodeling enzyme for 1 hour. Alternatively, the uterus is treated with the at least one ECM remodeling enzyme for 30 minutes Alternatively, the uterus is treated with the at least one ECM remodeling enzyme for 20 minutes. Alternatively, the uterus is treated with the at least one ECM remodeling enzyme for 10 minutes Alternatively, the uterus is treated with the at least one ECM remodeling enzyme for 9 minutes Alternatively, the uterus is treated with the at least one ECM remodeling enzyme for 8 minutes Alternatively, the uterus is treated with the at least one ECM remodeling enzyme for 7 minutes Alternatively, the uterus is treated with the at least one ECM remodeling enzyme for 6 minutes Alternatively, the uterus is treated with the at least one ECM remodeling enzyme for 5 minutes Alternatively, the uterus is treated with the at least one ECM remodeling enzyme for 4 minutes Alternatively, the uterus is treated with the at least one ECM remodeling enzyme for 3 minutes Alternatively, the uterus is treated with the at least one ECM remodeling enzyme for 2 minutes Alternatively, the uterus is treated with the at least one ECM remodeling enzyme for 1 minute.

In some embodiments, the uterus of the mammal is treated with the at least one ECM remodeling enzyme to 12 hours. In some embodiments, the t12 hour treatment is repeated three times.

In some embodiments, between 0.1 to 10000 ng of the at least one ECM remodeling enzyme is administered to the uterus of a mammal. In some embodiments, between 0.1 to 1000 ng of the at least one ECM remodeling enzyme is administered to the uterus of a mammal. In some embodiments, between 0.1 to 100 ng of the at least one ECM remodeling enzyme is administered to the uterus of a mammal. In some embodiments, between 0.1 to 80 ng of the at least one ECM remodeling enzyme is administered to the uterus of a mammal. In some embodiments, between 0.1 to 60 ng of the at least one ECM remodeling enzyme is administered to the uterus of a mammal. In some embodiments, between 0.1 to 40 ng of the at least one ECM remodeling enzyme is administered to the uterus of a mammal. In some embodiments, between 0.1 to 20 ng of the at least one ECM remodeling enzyme is administered to the uterus of a mammal. In some embodiments, between 0.1 to 15 ng of the at least one ECM remodeling enzyme is administered to the uterus of a mammal of an embryo. In some embodiments, between 0.1 to 10 ng of the at least one ECM remodeling enzyme is administered to the uterus of a mammal. In some embodiments, between 0.1 to 5 ng of the at least one ECM remodeling enzyme is administered to the uterus of a mammal. In some embodiments, between 0.1 to 1 ng of the at least one ECM remodeling enzyme is administered to the uterus of a mammal.

In some embodiments, between 0.5 $\mu$M to 50 $\mu$M of the at least one ECM remodeling enzyme is administered to the uterus of a mammal. In some embodiments, 0.5 $\mu$M of the at least one ECM remodeling enzyme is administered to the uterus of a mammal. In some embodiments, 0.5 $\mu$M of the at least one ECM remodeling enzyme is administered to the uterus of a mammal. In some embodiments, 0.5 $\mu$M of the at least one ECM remodeling enzyme is administered to the uterus of a mammal. In some embodiments, 1 $\mu$M of the at least one ECM remodeling enzyme is administered to the uterus of a mammal. In some embodiments, 2 $\mu$M of the at least one ECM remodeling enzyme is administered to the uterus of a mammal. In some embodiments, 3 $\mu$M of the at least one ECM remodeling enzyme is administered to the uterus of a mammal. In some embodiments, 4 $\mu$M of the at least one ECM remodeling enzyme is administered to the uterus of a mammal. In some embodiments, 5 $\mu$M of the at least one ECM remodeling enzyme is administered to the uterus of a mammal. In some embodiments, 6 $\mu$M of the at least one ECM remodeling enzyme is administered to the uterus of a mammal. In some embodiments, 7 $\mu$M of the at least one ECM remodeling enzyme is administered to the uterus of a mammal. In some embodiments, 8 $\mu$M of the at least one ECM remodeling enzyme is administered to the uterus of a mammal. In some embodiments, 9 $\mu$M of the at least one ECM remodeling enzyme is administered to the uterus of a mammal. In some embodiments, 10 $\mu$M of the at least one ECM remodeling enzyme is administered to the uterus of a mammal. In some embodiments, 20 $\mu$M of the at least one ECM remodeling enzyme is administered to the uterus of a mammal. In some embodiments, 30 $\mu$M of the at least one ECM remodeling enzyme is administered to the uterus of a mammal. In some embodiments, 40 $\mu$M of the at least one ECM remodeling enzyme is administered to the uterus of a mammal. In some embodiments, 50 $\mu$M of the at least one ECM remodeling enzyme is administered to the uterus of a mammal.

The volume that is administered into the uterus of the mammal is dependent on a number of factors, such as, for example, the species of mammal, the area of the uterus to be treated, the volume of the uterus, and the like. Thus, in some embodiments, the volume is sufficient to deliver the at least one ECM remodeling enzyme in an amount sufficient to remodel the ECM of the endometrium of the uterus. For example, by way of illustration, in the mouse, the volume is from 1 $\mu$l to 5 $\mu$l.

In some embodiments, between 1 to 20 ng of the at least one ECM remodeling enzyme is administered to the uterus of a mammal. In some embodiments, between 5 to 20 ng of the at least one ECM remodeling enzyme is administered to the uterus of a mammal. In some embodiments, between 10-20 ng of the at least one ECM remodeling enzyme is administered to the uterus of a mammal. In some embodiments, between 15-20 ng of the at least one ECM remodeling enzyme is administered to the uterus of a mammal. In some embodiments, between 5-15 ng of the at least one ECM remodeling enzyme is administered to the uterus of a mammal.

In some embodiments, 100% of the endometrium of the uterus is treated. In some embodiments, less than 100% of the endometrium of the uterus is treated. In some embodiments, 90% of the endometrium of the uterus is treated. In some embodiments, 80% of the endometrium of the uterus is treated. In some embodiments, 70% of the endometrium of the uterus is treated. In some embodiments, 60% of the endometrium of the uterus is treated. In some embodiments, 50% of the endometrium of the uterus is treated. In some embodiments, 40% of the endometrium of the uterus is treated. In some embodiments, 30% of the endometrium of the uterus is treated. In some embodiments, 20% of the endometrium of the uterus is treated. In some embodiments, 10% of the endometrium of the uterus is treated. In some embodiments, 9% of the endometrium of the uterus is treated. In some embodiments, 8% of the endometrium of the uterus is treated. In some embodiments, 7% of the endometrium of the uterus is treated. In some embodiments, 6% of the endometrium of the uterus is treated. In some embodiments, 5% of the endometrium of the uterus is treated. In some embodiments, 4% of the endometrium of the uterus is treated. In some embodiments, 3% of the endometrium of the uterus is treated. In some embodiments, 2% of the endometrium of the uterus is treated. In some embodiments, 1% of the endometrium of the uterus is treated.

In some embodiments, treatment of a uterus with the at least one ECM remodeling enzyme results in between a 10% to 50% increase in the rate of implantation of an embryo, compared to a non-treated uterus. In some embodiments, treatment of a uterus with the at least one ECM remodeling enzyme results in between a 15% to 50% increase in the rate of implantation of an embryo, compared to a non-treated uterus. In some embodiments, treatment of a uterus with the at least one ECM remodeling enzyme results in between a 20% to 50% increase in the rate of implantation of an embryo, compared to a non-treated uterus. In some embodiments, treatment of a uterus with the at least one ECM remodeling enzyme results in between a 25% to 50% increase in the rate of implantation of an embryo, compared to a non-treated uterus. In some embodiments, treatment of a uterus with the at least one ECM remodeling enzyme results in between a 30% to 50% increase in the rate of implantation of an embryo, compared to a non-treated uterus. In some embodiments, treatment of a uterus with the at least one ECM remodeling enzyme results in between a 35% to 50% increase in the rate of implantation of an embryo, compared to a non-treated uterus. In some embodiments, treatment of a uterus with the at least one ECM remodeling enzyme results in between a 40% to 50% increase in the rate of implantation of an embryo, compared to a non-treated uterus. In some embodiments, treatment of a uterus with the at least one ECM remodeling enzyme results in between a 45% to 50% increase in the rate of implantation of an embryo, compared to a non-treated uterus.

In some embodiments, treatment of a uterus with the at least one ECM remodeling enzyme results in a 4 fold increase in the rate of adhesion the at least one embryo to the ECM of the endometrium of the uterus, compared to a non-treated uterus. In some embodiments, treatment of a uterus with the at least one ECM remodeling enzyme results in a 3.9 fold increase in the rate of adhesion the at least one embryo to the ECM of the endometrium of the uterus, compared to a non-treated uterus. In some embodiments, treatment of a uterus with the at least one ECM remodeling enzyme results in a 3.8 fold increase in the rate of adhesion the at least one embryo to the ECM of the endometrium of the uterus, compared to a non-treated uterus. In some embodiments, treatment of a uterus with the at least one ECM remodeling enzyme results in a 3.7 fold increase in the rate of adhesion the at least one embryo to the ECM of the endometrium of the uterus, compared to a non-treated uterus. In some embodiments, treatment of a uterus with the at least one ECM remodeling enzyme results in a 3.6 fold increase in the rate of adhesion the at least one embryo to the ECM of the endometrium of the uterus, compared to a non-treated uterus. In some embodiments, treatment of a uterus with the at least one ECM remodeling enzyme results in a 3.5 fold increase in the rate of adhesion the at least one embryo to the ECM of the endometrium of the uterus, compared to a non-treated uterus. In some embodiments, treatment of a uterus with the at least one ECM remodeling enzyme results in a 3.4 fold increase in the rate of adhesion the at least one embryo to the ECM of the endometrium of the uterus, compared to a non-treated uterus. In some embodiments, treatment of a uterus with the at least one ECM remodeling enzyme results in a 3.3 fold increase in the rate of adhesion the at least one embryo to the ECM of the endometrium of the uterus, compared to a non-treated uterus. In some embodiments, treatment of a uterus with the at least one ECM remodeling enzyme results in a 3.2 fold increase in the rate of adhesion the at least one embryo to the ECM of the endometrium of the uterus, compared to a non-treated uterus. In some embodiments, treatment of a uterus with the at least one ECM remodeling enzyme results in a 3.1 fold increase in the rate of adhesion the at least one embryo to the ECM of the endometrium of the uterus, compared to a non-treated uterus. In some embodiments, treatment of a uterus with the at least one ECM remodeling enzyme results in a 3 fold increase in the rate of adhesion the at least one embryo to the ECM of the endometrium of the uterus, compared to a non-treated uterus. In some embodiments, treatment of a uterus with the at least one ECM remodeling enzyme results in a 2.9 fold increase in the rate of adhesion the at least one embryo to the ECM of the endometrium of the uterus, compared to a non-treated uterus. In some embodiments, treatment of a uterus with the at least one ECM remodeling enzyme results in a 2.8 fold increase in the rate of adhesion the at least one embryo to the ECM of the endometrium of the uterus, compared to a non-treated uterus. In some embodiments, treatment of a uterus with the at least one ECM remodeling enzyme results in a 2.7 fold increase in the rate of adhesion the at least one embryo to the ECM of the endometrium of the uterus, compared to a non-treated uterus. In some embodiments, treatment of a uterus with the at least one ECM remodeling enzyme results in a 2.6 fold increase in the rate of adhesion the at least one embryo to the ECM of the endometrium of the uterus, compared to a non-treated uterus. In some embodiments, treatment of a uterus with the at least one ECM remodeling enzyme results in a 2.5 fold increase in the rate of adhesion the at least one embryo to the ECM of the endometrium of the uterus, compared to a non-treated uterus. In some embodiments, treatment of a uterus with the at least one ECM remodeling enzyme results in a 2.4 fold increase in the rate of adhesion the at least one embryo to the ECM of the endometrium of the uterus, compared to a non-treated uterus. In some embodiments, treatment of a uterus with the at least one ECM remodeling enzyme results in a 2.3 fold increase in the rate of adhesion the at least one embryo to the ECM of the endometrium of the uterus, compared to a non-treated uterus. In some embodiments, treatment of a uterus with the at least one ECM remodeling enzyme results in a 2.2 fold increase in the rate of adhesion the at least one embryo to the ECM of the endometrium of the uterus, compared to a non-treated uterus. In some embodiments, treatment of a uterus with the at least one ECM remodeling enzyme results in a 2.1 fold increase in the rate of adhesion the at least one embryo to the ECM of the endometrium of the uterus, compared to a non-treated uterus. In some embodiments, treatment of a uterus with the at least one ECM remodeling enzyme results in a 2 fold increase in the rate of adhesion the at least one embryo to the ECM of the endometrium of the uterus, compared to a non-treated uterus. In some embodiments, treatment of a uterus with the at least one ECM remodeling enzyme results in a 1.9 fold increase in the rate of adhesion the at least one embryo to the ECM of the endometrium of the uterus, compared to a non-treated uterus. In some embodiments, treatment of a uterus with the at least one ECM remodeling enzyme results in a 1.8 fold increase in the rate of adhesion the at least one embryo to the ECM of the endometrium of the uterus, compared to a non-treated uterus. In some embodiments, treatment of a uterus with the at least one ECM remodeling enzyme results in a 1.7 fold increase in the rate of adhesion the at least one embryo to the ECM of the endometrium of the uterus, compared to a non-treated uterus. In some embodiments, treatment of a uterus with the at least one ECM remodeling enzyme results in a 1.6 fold increase in the rate of adhesion the at least one embryo to the ECM of the endometrium of the uterus, compared to a non-treated uterus. In some embodiments, treatment of a uterus with the at least one ECM remodeling enzyme results in a 1.5 fold increase in the rate of adhesion the at least one embryo to the ECM of the endometrium of the uterus, compared to a non-treated uterus. In some embodiments, treatment of a uterus with the at least one ECM remodeling enzyme results in a 1.4 fold increase in the rate of adhesion the at least one embryo to the ECM of the endometrium of the uterus, compared to a non-treated uterus. In some embodiments, treatment of a uterus with the at least one ECM remodeling enzyme results in a 1.3 fold increase in the rate of adhesion the at least one embryo to the ECM of the endometrium of the uterus, compared to a non-treated uterus. In some embodiments, treatment of a uterus with the at least one ECM remodeling enzyme results in a 1.2 fold increase in the rate of adhesion the at least one embryo to the ECM of the endometrium of the uterus, compared to a non-treated uterus. In some embodiments, treatment of a uterus with the at least one ECM remodeling enzyme results in a 1.1 fold increase in the rate of adhesion the at least one embryo to the ECM of the endometrium of the uterus, compared to a non-treated uterus.

In some embodiments, the present invention provides a method, wherein the method increases the rate of embryo implantation in the uterus of a mammal, the method comprising:
  a) contacting at least one embryo with at least one ECM remodeling enzyme selected from the group consisting of matrix metalloproteinase (MMP)-1, MMP-2, MMP-3, MMP-7, MMP-8 MMP-9, MMP-10, MMP-11, MMP-12, MMP-13, MMP-14, MMP-15, MMP-16, MMP-17, MMP-19, MMP-20, MMP-21, MMP-23, MMP-24, MMP-25, MMP-26, MMP-27, and MMP-28; and
  b) introducing at least one treated embryo into a treated uterus of a mammal and allowing the introduced embryo to implant.

In some embodiments, the at least one embryo is contacted with the at least one extra cellular matrix (ECM) remodeling enzyme at an amount sufficient to remodel the ECM of the at least one embryo.

In some embodiments, the at least one embryo is contacted with the at least one extra cellular matrix (ECM) remodeling enzyme for a time sufficient to remodel the ECM of the at least one embryo.

In some embodiments, the rate of implantation of the at least one embryo is greater following treatment of the at least one embryo with the ECM remodeling enzyme, compared to the rate of implantation a non-treated at least one embryo.

In some embodiments, the at least one embryo is treated with the at least one ECM remodeling enzyme for 12 hours. Alternatively, the at least one embryo is treated with the at least one ECM remodeling enzyme for 10 hours. Alternatively, the at least one embryo is treated with the at least one ECM remodeling enzyme for 9 hours. Alternatively, the at least one embryo is treated with the at least one ECM remodeling enzyme for 8 hours. Alternatively, the at least one embryo is treated with the at least one ECM remodeling enzyme for 7 hours. Alternatively, the at least one embryo is treated with the at least one ECM remodeling enzyme for 6 hours. Alternatively, the at least one embryo is treated with the at least one ECM remodeling enzyme for 5 hours. Alternatively, the at least one embryo is treated with the at least one ECM remodeling enzyme for 4 hours. Alternatively, the at least one embryo is treated with the at least one ECM remodeling enzyme for 3 hours. Alternatively, the at least one embryo is treated with the at least one ECM remodeling enzyme for 2 hours. Alternatively, the at least one embryo is treated with the at least one ECM remodeling enzyme for 1 hour. Alternatively, the at least one embryo is treated with the at least one ECM remodeling enzyme for 30 minutes Alternatively, the at least one embryo is treated with the at least one ECM remodeling enzyme for 20 minutes Alternatively, the at least one embryo is treated with the at least one ECM remodeling enzyme for 10 minutes Alternatively, the at least one embryo is treated with the at least one ECM remodeling enzyme for 9 minutes Alternatively, the at least one embryo is treated with the at least one ECM remodeling enzyme for 8 minutes Alternatively, the at least one embryo is treated with the at least one ECM remodeling enzyme for 7 minutes Alternatively, the at least one embryo is treated with the at least one ECM remodeling enzyme for 6 minutes Alternatively, the at least one embryo is treated with the at least one ECM remodeling enzyme for 5 minutes Alternatively, the at least one embryo is treated with the at least one ECM remodeling enzyme for 4 minutes Alternatively, the at least one embryo is treated with the at least one ECM remodeling enzyme for 3 minutes Alternatively, the at least one embryo is treated with the at least one ECM remodeling enzyme for 2 minutes Alternatively, the at least one embryo is treated with the at least one ECM remodeling enzyme for 1 minute.

In some embodiments, treatment of the at least one embryo with the at least one ECM remodeling enzyme results in between a 10% to 50% increase in the rate of implantation of the at least one embryo, compared to a non-treated embryo. In some embodiments, treatment of the at least one embryo with the at least one ECM remodeling enzyme results in between a 15% to 50% increase in the rate of implantation of the at least one embryo, compared to a non-treated embryo. In some embodiments, treatment of the at least one embryo with the at least one ECM remodeling enzyme results in between a 20% to 50% increase in the rate of implantation of the at least one embryo, compared to a non-treated embryo. In some embodiments, treatment of the at least one embryo with the at least one ECM remodeling enzyme results in between a 25% to 50% increase in the rate of implantation of the at least one embryo, compared to a non-treated embryo. In some embodiments, treatment of the at least one embryo with the at least one ECM remodeling enzyme results in between a 30% to 50% increase in the rate of implantation of the at least one embryo, compared to a non-treated embryo. In some embodiments, treatment of the at least one embryo with the at least one ECM remodeling enzyme results in between a 35% to 50% increase in the rate of implantation of the at least one embryo, compared to a non-treated embryo. In some embodiments, treatment of the at least one embryo with the at least one ECM remodeling enzyme results in between a 40% to 50% increase in the rate of implantation of the at least one embryo, compared to a non-treated embryo. In some embodiments, treatment of the at least one embryo with the at least one ECM remodeling enzyme results in between a 45% to 50% increase in the rate of implantation of the at least one embryo, compared to a non-treated embryo.

The At Least One Extracellular Matrix Remodeling Enzyme

In some embodiments, the at least one ECM remodeling enzyme is a matrix metalloproteinase (MMP). The MMP may be recombinant, or purified from an animal.

In some embodiments, the MMP is selected from the group consisting of: MMP-1, MMP-2, MMP-3, MMP-7, MMP-8 MMP-9, MMP-10, MMP-11, MMP-12, MMP-13, MMP-14, MMP-15, MMP-16, MMP-17, MMP-19, MMP-20, MMP-21, MMP-23, MMP-24, MMP-25, MMP-26, MMP-27, and MMP-28.

In some embodiments, the at least one ECM remodeling enzyme includes MMP-1. Alternatively, in some embodiments, the at least one ECM remodeling enzyme includes MMP-2. Alternatively, in some embodiments, the at least one ECM remodeling enzyme includes MMP-3. Alternatively, in some embodiments, the at least one ECM remodeling enzyme includes MMP-7. Alternatively, in some embodiments, the at least one ECM remodeling enzyme includes MMP-8. Alternatively, in some embodiments, the at least one ECM remodeling enzyme includes MMP-9. Alternatively, in some embodiments, the at least one ECM remodeling enzyme includes MMP-10. Alternatively, in some embodiments, the at least one ECM remodeling enzyme includes MMP-11. Alternatively, in some embodiments, the at least one ECM remodeling enzyme includes MMP-12. Alternatively, in some embodiments, the at least one ECM remodeling enzyme includes MMP-13. Alternatively, in some embodiments, the at least one ECM remodeling enzyme includes MMP-14. Alternatively, in some embodiments, the at least one ECM remodeling enzyme includes MMP-15. Alternatively, in some embodiments, the at least one ECM remodeling enzyme includes MMP-16. Alternatively, in some embodiments, the at least one ECM remodeling enzyme includes MMP-17. Alternatively, in some embodiments, the at least one ECM remodeling enzyme includes MMP-19. Alternatively, in some embodiments, the at least one ECM remodeling enzyme includes MMP-20. Alternatively, in some embodiments, the at least one ECM remodeling enzyme includes MMP-21. Alternatively, in some embodiments, the at least one ECM remodeling enzyme includes MMP-23. Alternatively, in some embodiments, the at least one ECM remodeling enzyme includes MMP-24. Alternatively, in some embodiments, the at least one ECM remodeling enzyme includes MMP-25. Alternatively, in some embodiments, the at least one ECM remodeling enzyme includes MMP-26. Alternatively, in some embodiments, the at least one ECM remodeling enzyme includes MMP-27. Alternatively, in some embodiments, the at least one ECM remodeling enzyme includes MMP-28.

In some embodiments, the MMP is MMP-1. Alternatively, in some embodiments, the MMP is MMP-2. Alternatively, in some embodiments, the MMP is MMP-3. Alternatively, in some embodiments, the MMP is MMP-7. Alternatively, in some embodiments, the MMP is MMP-8. Alternatively, in some embodiments, the MMP is MMP-9. Alternatively, in some embodiments, the MMP is MMP-10. Alternatively, in some embodiments, the MMP is MMP-11. Alternatively, in some embodiments, the MMP is MMP-12. Alternatively, in some embodiments, the MMP is MMP-13. Alternatively, in some embodiments, the MMP is MMP-14. Alternatively, in some embodiments, the MMP is MMP-15. Alternatively, in some embodiments, the MMP is MMP-16. Alternatively, in some embodiments, the MMP is MMP-17. Alternatively, in some embodiments, the MMP is MMP-19. Alternatively, in some embodiments, the MMP is MMP-20. Alternatively, in some embodiments, the MMP is MMP-21. Alternatively, in some embodiments, the MMP is MMP-23. Alternatively, in some embodiments, the MMP is MMP-24. Alternatively, in some embodiments, the MMP is MMP-25. Alternatively, in some embodiments, the MMP is MMP-26. Alternatively, in some embodiments, the MMP is MMP-27. Alternatively, in some embodiments, the MMP is MMP-28.

In some embodiments, the at least one ECM remodeling enzyme is formulated as a pharmaceutical composition for inter-uterine application. In some embodiments, the pharmaceutical composition further comprises a carrier, such as, for example, a saline solution, approved for intra-uterine application.

In some embodiments, the pharmaceutical composition may also include additional active ingredients, such as, but not limited to, leukocyte inhibitory factor (LIF). In some embodiments, the additional factors include products of the digestion of ECM with an at least one ECM remodeling enzyme.

In some embodiments, the pharmaceutical composition is contained in a container or dispenser adapted for intrauterine application. Such containers include, for example an elongated neck or dispenser capable of reaching the uterus via the vagina and cervix.

In some embodiments, the pharmaceutical composition is administered via an intrauterine catheter.

In some embodiments, the uterus is exposed surgically, wherein an opening is made in the uterus, and the pharmaceutical composition is introduced through the opening.

In some embodiments, the pharmaceutical composition comprises a vaginal suppository.

In some embodiments, the pharmaceutical composition comprises a foam, a gel, a sponge, a capsule, a matrix, and the like.

Screening

In some embodiments, test compounds, comprising compounds or enzymes, that remodel ECM and increase the rate of embryo implantation are identified by treating isolated uteri with the test compound, and determining the number of adherent cells, such as, for example, rat-1 cells that adhere to the treated uteri. In some embodiments the amount of cells adhered to treated uteri can be compared to control, or non-treated uteri. An example of a screen that employs adherent cells and isolated uteri is described in Example 9 below.

In some embodiments, test compounds, comprising compounds or enzymes, that remodel ECM and increase the rate of embryo implantation are identified by treating isolated uteri with the test compound, and determining the number of oocytes that adhere to the treated uteri. In some embodiments the amount of oocytes adhered to treated uteri can be compared to control, or non-treated uteri. An example of a screen that employs oocytes and isolated uteri is described in Example 9 below.

In some embodiments, test compounds, comprising compounds or enzymes, that remodel ECM and increase the rate of embryo implantation are identified by treating isolated uteri with the test compound, and determining the number of embryos that adhere to the treated uteri. In some embodiments the amount of embryos adhered to treated uteri can be compared to control, or non-treated uteri. An example of a screen that employs embryos and isolated uteri is described in Example 9 below.

In some embodiments, test compounds, comprising compounds or enzymes, that remodel ECM and increase the rate of embryo implantation are identified by treating isolated ECM fascicles with the test compound, and determining the number of adherent cells, such as, for example, rat-1 cells that adhere to the treated ECM fascicles. In some embodiments the amount of cells adhered to treated ECM fascicles can be compared to control, or non-treated ECM fascicles. An example of a screen that employs adherent cells and isolated ECM fascicles is described in Example 9 below.

In some embodiments, test compounds, comprising compounds or enzymes, that remodel ECM and increase the rate of embryo implantation are identified by treating isolated ECM fascicles with the test compound, and determining the number of oocytes that adhere to the treated ECM fascicles. In some embodiments the amount of oocytes adhered to treated ECM fascicles can be compared to control, or non-treated ECM fascicles. An example of a screen that employs oocytes and isolated ECM fascicles is described in Example 9 below.

In some embodiments, test compounds, comprising compounds or enzymes, that remodel ECM and increase the rate of embryo implantation are identified by treating isolated ECM fascicles with the test compound, and determining the number of embryos that adhere to the treated ECM fascicles. In some embodiments the amount of embryos adhered to treated ECM fascicles can be compared to control, or non-treated ECM fascicles. An example of a screen that employs embryos and isolated ECM fascicles is described in Example 9 below.

Reference is now made to the following examples, which together with the above descriptions illustrate some embodiments of the invention in a non-limiting fashion.

EXAMPLES

Example 1: Adhesion of Murine Oocytes and Murine Embryos to ECM was Increased Following Treatment of ECM with MMP-1 According to Some Embodiments of the Present Invention Preparation of Human MMP-1

Human proMMP1 was cloned in the pET3a expression vector. Bacteria were grown in LB Broth sterile medium (1 L containing 10 g Bacto-tryptone, 5 g yeast extract, 10 g NaCl, pH 7.5) with 150 µg/mL of ampicillin at 37° C. Protein expression was induced with 0.4 mM isopropyl-b-D-thiogalactoside at an OD600=0.6, and growth was allowed to continue for a further 4 h. Following expression, the enzyme accumulated in the fraction of inclusion bodies. All steps and refolding of proMMP1 were performed at 4° C. unless noted. The cells from 1 L of the culture (approximately 16 g) were then harvested by centrifugation (3500×g, Sorvall LYNX4000 centrifuge, 15 min) and resuspended in 100 mL of lysis buffer (50 mM Tris, pH 8.5, 0.1M NaCl, 5 mM β-mercaptoethanol, 2 mM EDTA, 0.1% Brij-35 mM, containing 1 pill of Complete (EDTA-free) protease cocktail (Boehringer Mannheim). The cells were then passed through a hand homogenizer, and after addition of approximately 10 mg lysozyme, stirred for 10-20 min in cold room. The suspension was then sonicated (6 cycles of 10 sec and 20 sec off at 65% of Virsonic 60 power amplitude) and centrifuged at 27000×g (Sorvall LYNX4000) for 40 min. The pellet was further suspended in 100 mL of buffer containing 50 mM Tris, pH 8.0, 2 M NaCl, 5 mM β-mercaptoethanol, 2 mM EDTA, 0.1% Brij-35, 100 mM $MgCl_2$) in the presence of 10-20 µL of 10 mg/mL of Dnase with 100 mM $MgCl_2$, sonicated as described above until the sample lost its viscosity and collected as before. After the centrifugation at 27000×g for 40 min, the washing procedure was repeated and the pellet was suspended with 100 mL buffer containing 50 mM TRIS, pH 8.0, 5 mM β-mercaptoethanol, passed over hand homogenizer and centrifugation at 27000×g for 40 min. The pellet, containing inclusion bodies was then solubilized in 25 mL of denaturation buffer (50 mM Tris, pH 8.0, 20 mM DTT, 50 mM $ZnCl_2$, 1 mM AHA, 8 M urea), stirred over night at room temperature and filtered through a 0.2 µm filter. The urea-extract of protein was further purified on Hi-Trap monoQ (GE Healthcare) 5 mL column in FPLC ACTA, using a gradient of 500 mM NaCl/25 min concentration (buffer A: 6 M urea, 20 mM Tris, pH 8.0 and buffer B: 6 M urea, 20 mM Tris, pH 8.0, 1 M NaCl). Fractions containing MMP1 were diluted to 75 µg/mL at room temperature using buffer (20 mM Tris, pH 8.0, 20 mM cystamine, 6 M urea) and then dialyzed against 5-8 L of 50 mM Tris, pH 8.0, 2 mM AHA, 1 mM hydroxyethylsulfate, 4 M urea, 5 mM $CaCl_2$, 0.1 mM $ZnCl_2$, 300 mM NaCl, 5 mM β-mercapthethanol, 4 M Urea at 4° C. overnight under stirring. The next steps of refolding were done against 2 M Urea, 50 mM Tris pH 8.0, 10 mM $CaCl_2$, 0.1 mM $ZnCl_2$, 300 mM NaCl, 2 mM AHA overnight, under stirring at 4° C. and 50 mM Tris pH 8.0, 10 mM $CaCl_2$, 0.1 mM $ZnCl_2$, 300 mM NaCl, 2 mM AHA.

The renatured proteins were then filtrated through 0.2 µm, concentrated to approximately 10 mL by Amicon cell (Millipore) with 10MWCO PES membrane and purified by size-exclusion chromatography using Superdex 75 26/60 (GE Healthcare) pre-equilibrated with 50 mM TRIS pH 8.0, 300 mM NaCl, 10 mM $CaCl_2$. The fraction eluted at 130-155 mL of SEC column was concentrated to ~3-5 µM and was stored at −80° C. in TNC with 10% glycerol.

Preparation of Human MMP-13

Human proMMP13 was cloned in the pCEP4 expression vector. HEK293 EBNA cells contain a pCEP4 expression plasmid with FLAG-proMMP13. The cells were initially grown on DMEM 10% FCS with penicillin/streptomycin. Once the cells had begun to divide, Geneticin (Sigma G418) was added to adjust the concentration of 250 µg/L (for EBNA-1 expressing cells). The cells were selected for Hygromycin B resistance medium containing 1000 µg/mL Hygromycin B. The cells were passaged twice a week. When the cells were confluent in 15 cm dishes, the medium was replaced to DMEM, containing penicillin/strep and 0.2% LEH (lactalbumin enzymatic hydrolysate; basic amino acids, Sigma L9010). The medium was collected once a week and centrifuged to remove cell debris and was frozen at −20° C. The yield for Hag-tagged-proMMP13 from 1 L of medium is about 0.7 mg.

A hand-made 2-3 mL column with the resin flag was equilibrated with TNC buffer (50 mM TRIS pH 7.5, 150 mM NaCl, 10 mM CaCl$_2$) and collected medium was loaded with flow rate of 1-1.5 mL/min. The column was then washed by TNC buffer, followed by 50 mM TRIS pH 7.5, 1 M NaCl, 10 mM CaCl$_2$ and washed by TNC. The protein was eluted with 3×5 mL Flag peptide (0.2 mg/mL in TNC). Eluated solution was concentrated to 2-5 mL and loaded on Superdex 200 16/60 gel filtration column (GE Healthcare) in TNC buffer. The higher molecular weight peak shoulder on the main peak corresponds to proMMP13-TIMP1 complex. ProMMP13 is eluted at 72-75 mL of column volume and was stored at −80° C. in TNC with 10% glycerol.

Activation of pro-MMP-1 and proMMP13

MMP1 and MMP13 were activated with 1 mM APMA (4-aminophenylmercuric acetate) in TNC buffer (50 mM-TrisHCl pH 7.5, 150 mM NaCl, 10 mM CaCl$_2$, 0.02% NaN$_3$) at 37° C. for 60 min and enzymatic activity was tested.

Preparation of Fascicle-Derived ECM

Fascicle-derived ECM was prepared from adult Norwegian rat-tails (3-6 months). Specifically, rat-tails were dissected, tendon fascicles (diameter approximately 0.6 mm) were gently extracted and extensively washed in TNC buffer (50 mM TRIS, pH 7.4, 150 mM NaCl, 10 mM CaCl$_2$, 0.02% NaN$_3$) to remove the macroscopic debris of tissue and the excess proteases. The samples were then flash frozen and kept at −80° C. until processed. Digested ECM samples were prepared by incubation of the fascicles in 500 nM MMP-1 or MMP-13 in TNC buffer at 30° C. for 24 h. Reactions were stopped by the addition of 20 mM EDTA pH 8.0. The ECM samples were then gently washed with double deionized water with following washing (at least three times) in a suitable buffer.

Figure 1B:
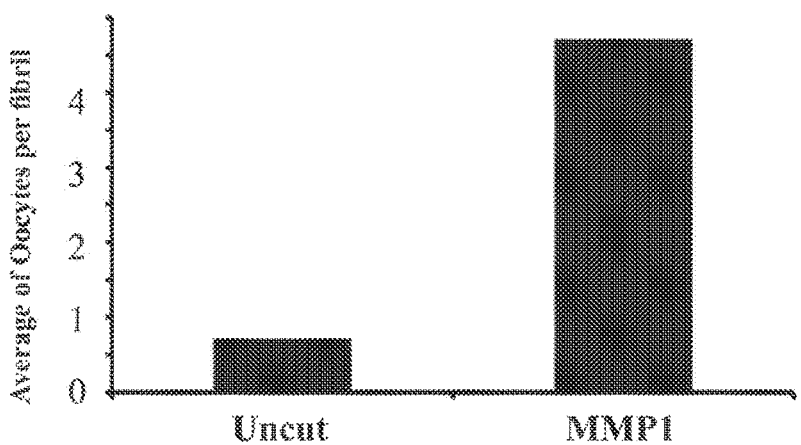

Facile-derived ECM, either intact or remodeled, were washed twice with PBS and then with DMEM and placed culture plates. Murine oocytes were added to the culture plates, incubated for up to 4 h at 37° C. and visualized using an optical microscope (Olympus SZX16-4× magnification). The results are shown in FIG. 1. FIGS. 1A and 1B shows an increase in the number of oocytes that adhered to remodeled ECM as compared with intact ECM. Therefore, murine oocytes adhered to an ECM pretreated with MMP1 (i.e., a remodeled ECM) at an increased rate (i.e., 4× more oocytes were observed to adhere per ECM remodeled fibril) compared with an untreated ECM.

Figure 2A:
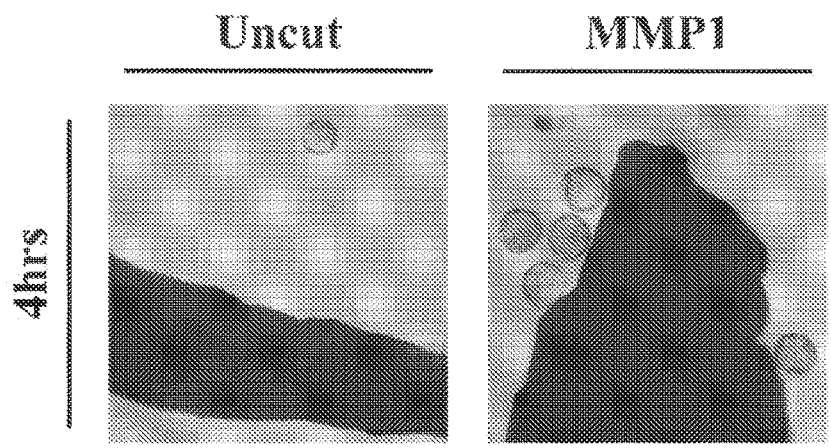
FIGS. 2A-2B.
Figure 2B:
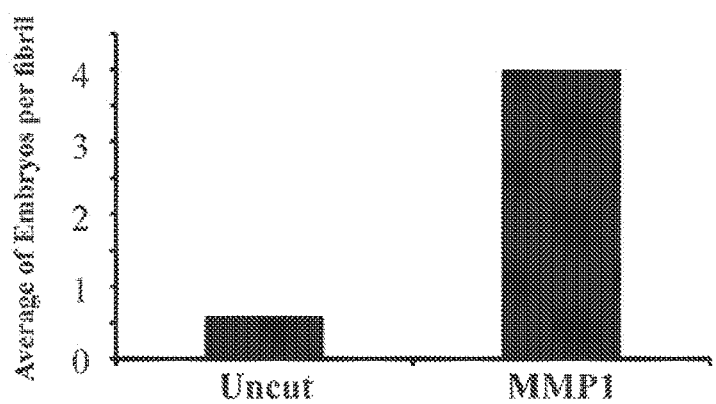

In a separate experiment, murine embryos were added to culture plates containing facile-derived ECM (intact or remodeled via treatment with MMP-1), and incubated for up to 4 h at 37° C. and visualized using an optical microscope. FIGS. 2A and 2B show an increase in the number of embryos that adhered to remodeled ECM as compared with intact ECM. Therefore, murine oocytes adhered to an ECM pretreated with MMP1 (i.e., a remodeled ECM) at an increased rate (i.e., 4× more embryos were observed to adhere per ECM remodeled fibril) compared with an untreated ECM.

Example 2: Implantation of Murine Embryos via IVF was Increased in Uteri Treated with Either MMP-1 or MMP-13 According to Some Embodiments of the Present Invention, Compared to Control All research was IACUC-approved. Vasectomized male (age 14 weeks) and female (age 10 weeks) Institute of Cancer Research ("ICR") mice were mated at a ratio of 1:2 to achieve pseudopregnancy. Prior to mating, male mice were housed individually, and females were housed 3 to 5 per cage in animal rooms maintained at 20 to 22° C. with an average relative humidity of 35% under a 12:12-hours light:dark cycle). After mating, female mice were checked each morning for copulation plugs. Female mice presenting plugs were removed from the mating cage and housed together at 3-5 mice per cage. Pseudopregnant mice at 2.5 days postcoitum (dpc) were randomly assigned into experimental groups: control or enzymatic treatment.

Surgical Embryo Transfer

Figure 3:
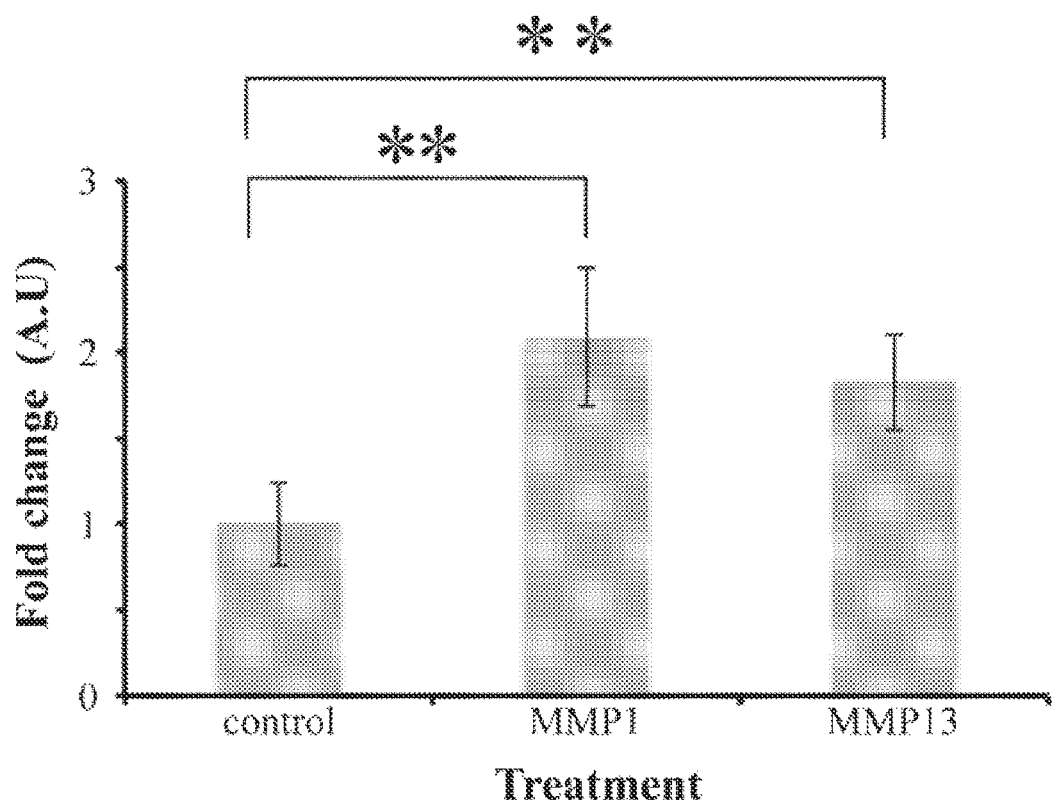
FIG. 3 shows the effect of treatment of murine uteri according to some embodiments of the present invention on the implantation of embryos via IVF. Results are shown as the fold increase in the number of embryos implanted in uteri treated with MMP-1 (MMP1), or MMP-13 (MMP13), compared to control animals (control). (n=30 for each group, p value less than 0.01).

Each pseudopregnant mouse was anesthetized with Ketamine/Xylazine (100 mg/kg). The incision site was shaved and disinfected, and an incision was made along the dorsal side of the mouse. The ovarian fat pad, ovary, oviduct, and upper uterine horn were exteriorized, and a small hole was made in the uterine horn by using a 26-gauge needle, following treatment with MMP-1 (MMP1 or TNC buffer (control group) for 10 minutes then the embryos were transferred from donor ICR mice into the pseudopregnant mice (10 embryos per mice). The organs were placed back into the body cavity, and wound clips were used to close the incision site. Mice were allowed to recover in a clean cage for additional 4 days and the number of implanted embryos were counted and recorded on day E6.5. The results are shown in FIG. 3. Pretreatment of uteri with MMP-1 for 10 minutes resulted in a 2-fold increase in the number of embryos implanted via IVF, compared to control. Similarly, pretreatment of uteri with MMP-13 for 10 minutes resulted in a 1.8-fold increase in the number of embryos implanted via IVF, compared to control.

In a separate experiment, pseudo pregnant mice were treated with MMP-7. However, none of the mice survived. This may have been due to infection, or, alternatively, due to the administration of MMP-7 itself.

Example 3: Implantation of Endogenous Murine Embryos was Increased in Uteri Treated with MMP-1 According to Some Embodiments of the Present Invention, Compared to Control All research was IACUC-approved. Male (age 14 weeks) and female (age 10 weeks) Institute of Cancer Research ("ICR") mice were mated at a ratio of 1:2. Prior to mating, male mice were housed individually, and females were housed 3 to 5 per cage in animal rooms maintained at 20 to 22° C. with an average relative humidity of 35% under a 12:12-hours light:dark cycle). 2 female mice were placed with a male mouse in a single cage for mating. Female mice were checked each morning for copulation plugs, females with plugs were removed from the mating cage and housed together at 3-5 mice per cage. On E2.5, female mice were placed on a wire-top cage and the small and large specula (ParaTechs) were placed sequentially into the vagina to open and expose the cervix. The NSET catheter (Paratech) then was inserted through the large speculum, past the cervical opening, and into the uterine horn allowing the administration of 5 μM of MMP1 or TNC buffer, the device and specula were removed, and the mice returned to their cage. Mice were allowed to recover in a clean cage for additional 4 days and the number of implanted embryos were counted and recorded on day E6.5 (n=20 for each group, p value less than 0.01). The results are shown in FIG. 4A and FIG. 4B.

Figure 4A:
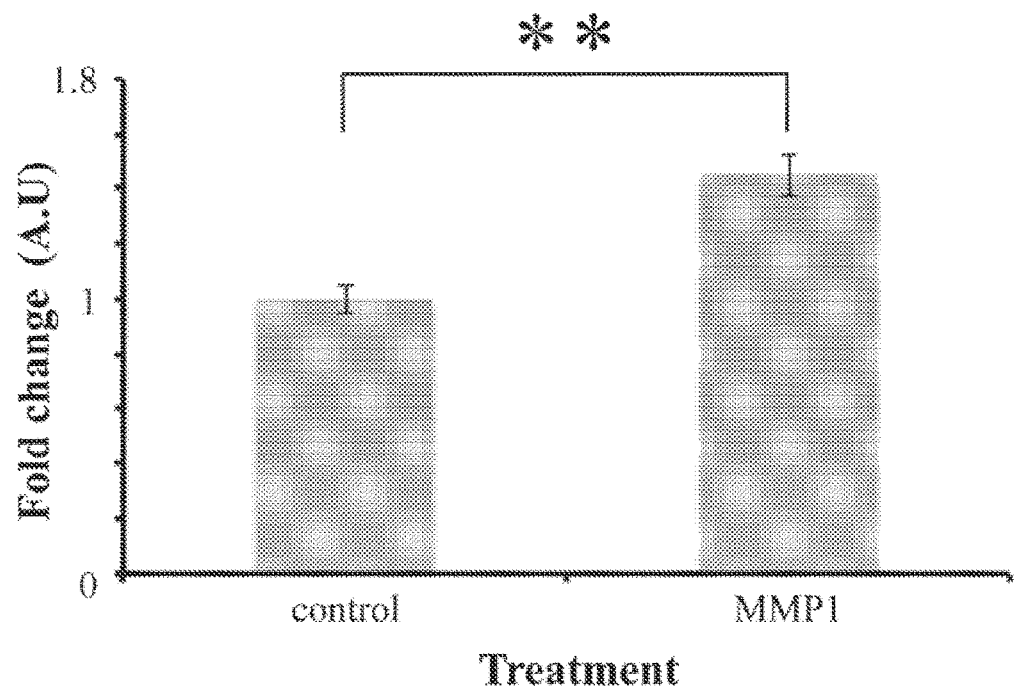
FIGS. 4A-4B show the effect of treatment of murine uteri according to some embodiments of the present invention on the implantation of embryos following copulation.
Figure 4B:
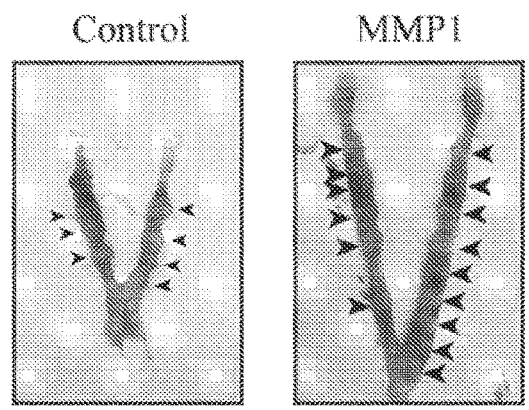

FIG. 4A shows an increase of endogenous embryo implantation (embryos formed via natural conception) into uteri treated with MMP-1 of 55%, compared to control uteri. FIG. 4B shows micrographs of embryos implanted in a murine uterus treated with MMP-1 according to some embodiments of the present invention (MMP1), and an untreated murine uterus (control). The positions of the implanted embryos are indicated by arrows.

Figure 5A:
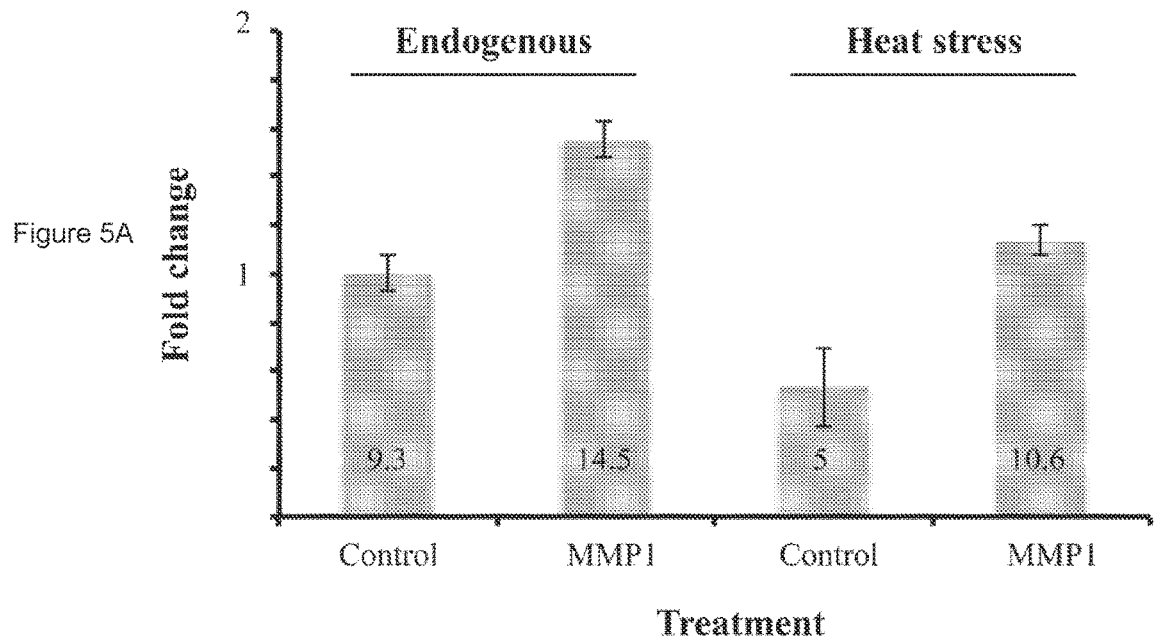
FIGS. 5A-5B show the effect of treatment of murine uteri according to some embodiments of the present invention on the implantation of endogenous embryos following copulation.

Example 4: Implantation of Endogenous Murine Embryos was Increased in Uteri Treated with MMP-1 According to Some Embodiments of the Present Invention, Compared to Control All research was IACUC-approved. Male (age 14 weeks) and female (age 10 weeks) Institute of Cancer Research ("ICR") mice were mated at a ratio of 1:2. Prior to mating, male mice were housed individually, and females were housed 3 to 5 per cage in animal rooms maintained at 20 to 22° C. with an average relative humidity of 35% under a 12:12-hours light:dark cycle). 2 female mice were placed with a male mouse in a single cage for mating. Female mice were checked each morning for copulation plugs, females with plugs were removed from the mating cage and housed together at 3-5 mice per cage. On E2.5, female mice were placed on a wire-top cage and the small and large specula (ParaTechs) were placed sequentially into the vagina to open and expose the cervix. The NSET catheter then was inserted through the large speculum, past the cervical opening, and into the uterine horn allowing the administration of 5 µM of MMP1 or TNC buffer, the device and specula were removed, and the mice returned to their cage. The cages were either placed in a pre-heated habitat at 38 C for 4 days, or in a habitat under control conditions (n=10 per housing group). Mice were sacrificed at day E6.5, and the number of implanted embryos were counted and recorded. The results are shown in FIG. 5A and FIG. 5B.

Figure 5B:
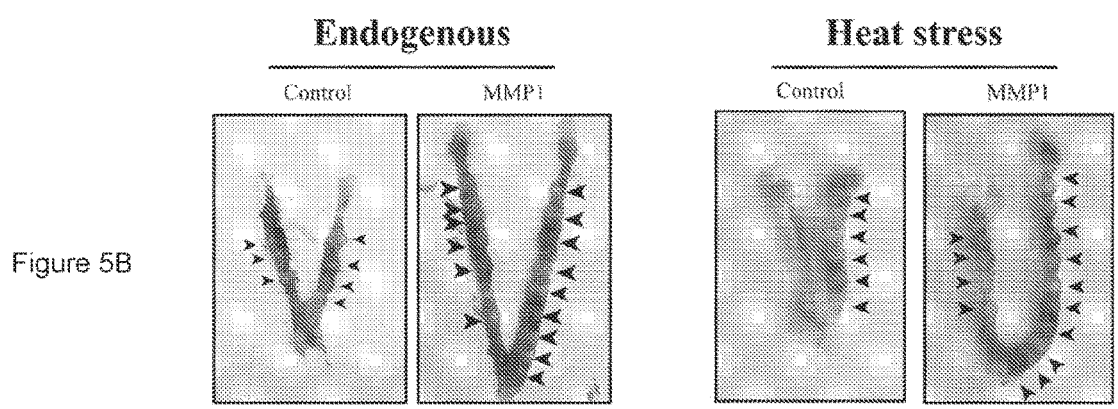

FIG. 5 shows the effect of treatment of murine uteri according to some embodiments of the present invention on the implantation of endogenous embryos following copulation. FIG. 5 A shows the fold increase in the number of endogenous embryos implanted in uteri treated with MMP-1 (MMP1), compared to control animals (control) under normal conditions (Endogenous), or heat stress conditions (Heat Stress). n=10 per treatment group. FIG. 5B shows micrographs of endogenous embryos implanted in a murine uterus treated with MMP-1 according to some embodiments of the present invention, under heat stress (heat stress), and a murine uterus treated with MMP-1 according to some embodiments of the present invention, under normal conditions (endogenous). The positions of the implanted embryos are indicated by arrows.

The data show that heat stress caused a 47% decrease in the number of embryos implanted. However, treatment of uteri with MMP-1 blocked the decrease in implantation caused by heat stress.

Example 5: Treatment of ECM According to Some Embodiments of the Present Invention Alters Cellular Properties The expression profiles of multiple and possibly redundant matrix remodeling proteases (e.g. collagenases) strongly differ in health, disease and development. Although enzymatic redundancy might be inferred from their close similarity in structure, their in vivo activity can lead to extremely diverse tissue-remodeling outcomes. We observed that proteolysis of collagen-rich natural extracellular matrix (ECM), generated uniquely by individual homologous proteases, leads to specific combinatorial events, which eventually affects overall ECM topography, visco-elastic properties and composition. We reveal differences in the movement and signaling patterns, morphology, and gene expression profiles of cells interacting with natural collagen-rich ECM degraded by different collagenases.

Thus, unlike envisioned before, matrix-remodeling systems are not redundant and give rise to precise ECM-cell crosstalk. As ECM proteolysis is an abundant biochemical process critical to tissue homoeostasis, these results improve our fundamental understanding of combinatorial factors dictating cell behavior.

Extracellular matrix (ECM) proteolysis is an abundant biochemical process. Our findings introduce a novel description of the multi-layered biological complexity generated by structurally homologous collagenases (MMP-1 and MMP-13) in collagen-rich, native ECM, one that may prove central to tissue homeostasis and pathology. The combinatorial events induced by these two collagenases, generates microenvironments characterized by distinct chemical, biomechanical and morphological ECM properties which further leads to differential cellular behaviors. Our findings might be used as a tool to further study ECM-related drug design.

The function and integrity of the ECM is vital for cell behavior, as well as for whole tissue homeostasis. The ECM undergoes constant remodeling during health and disease states. Components are regularly being deposited, degraded or otherwise modified. The highly stable fibrillar collagen type I (Col I) is abundant in many organ-derived ECMs and connective tissues; it serves as a tissue scaffold, determining ECM mechanical properties and anchoring other ECM proteins necessary for cell function. These processes are orchestrated by multiple remodeling enzymes among which the matrix metalloproteinase (MMP) family plays an important role. Only a few members of this proteinase family, the collagenases, are able to degrade the resistant fibrillar collagens, i.e., Col I as well as other ECM molecules. The colleganases have conserved amino acids in their zinc-containing catalytic domain and show high structural similarities (as reflected in their functional domain organization). Nevertheless, the complex effects exerted by different MMPs on ECM and cells in vivo remain poorly understood.

The enzymatic activity of MMPs and, specifically collagenases in vivo is tightly regulated, with enzymatic dysregulation causing irreversible damage, associated with a variety of diseases. Abnormally elevated levels of MMP-1 or both MMP-1 and MMP-13 have been associated with different types of cancers, as well as inflammatory diseases.

Here we collectively profiled the unique remodeling events caused by two secreted collagenases (MMP-1 and MMP-13) by using biochemical, physical and proteomics tools. We show that these proteases drive morphological biochemical and visco-elastic ECM changes leading to unique ECM-cell crosstalk. We reveal that MMP-1 and MMP-13 cause distinct ECM degradation, bringing about significantly distinct cellular phenotypes. Our findings show the combinatorial complexity and selectivity of collagenase-associated degradation mechanisms during tissue remodeling, which could be used as a tool for future therapeutic interventions.

Selective Degradation of ECM by Collagenases Determines Fibroblast Behavior

Figure 6A:
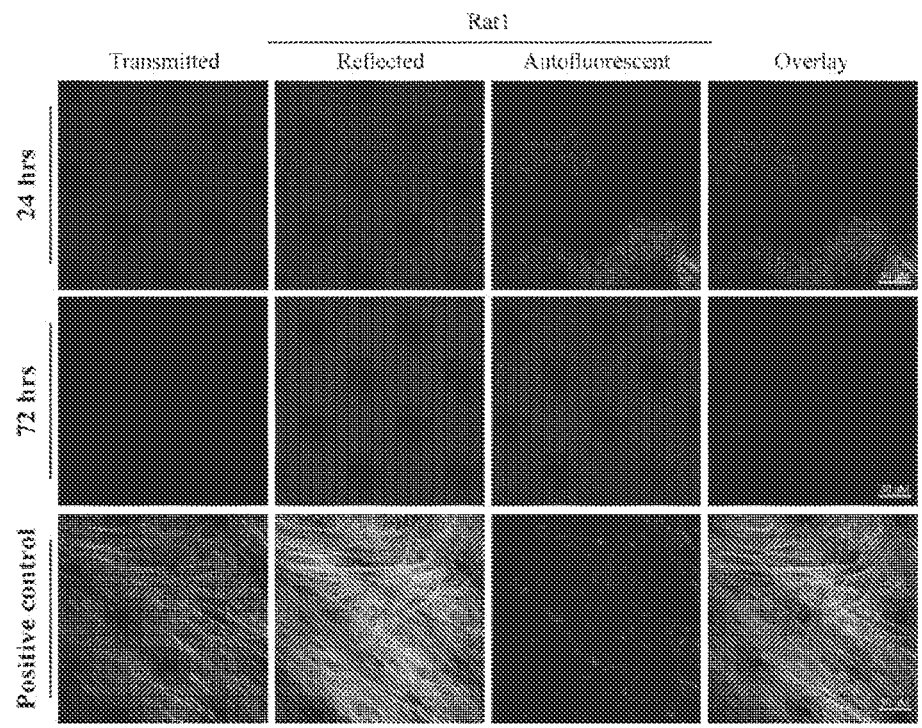
FIGS. 6A-6B show the detection of collagen deposition or MMP-1 and MMP-13 secretion in rat-1 fibroblasts.
Figure 6B:
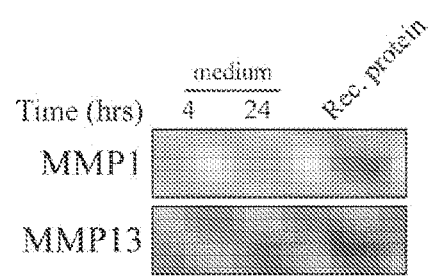

We set out to characterize the specific influences of the highly abundant collagenases on fibroblasts-ECM crosstalk. In this study we used natural collagen fascicles from tendons of 6-month-old rats as a simplified model of ECM. The ECM of tendon is composed of 60-85% collagens, where Col I is the most abundant variant. Other components include proteoglycans (PG) and glycoproteins (GP). Collagen molecules in fascicles are organized into precisely aligned hierarchical structures (e.g., microfibrils, fibrils, fibers). Since fibroblast cell lines inherently express ECM proteins and remodeling enzymes, we conducted our experiments at the early stages of interactions (up to 4 hours), in this time frame, no collagen deposition or MMP-1 and MMP-13 secretion was detected (See FIG. 6). We were thus able to isolate the specific effect of exogenously added remodeling enzymes on the ECM, excluding stimuli arising from soluble ECM signaling molecules and bio-active fragments.

Figure 7:
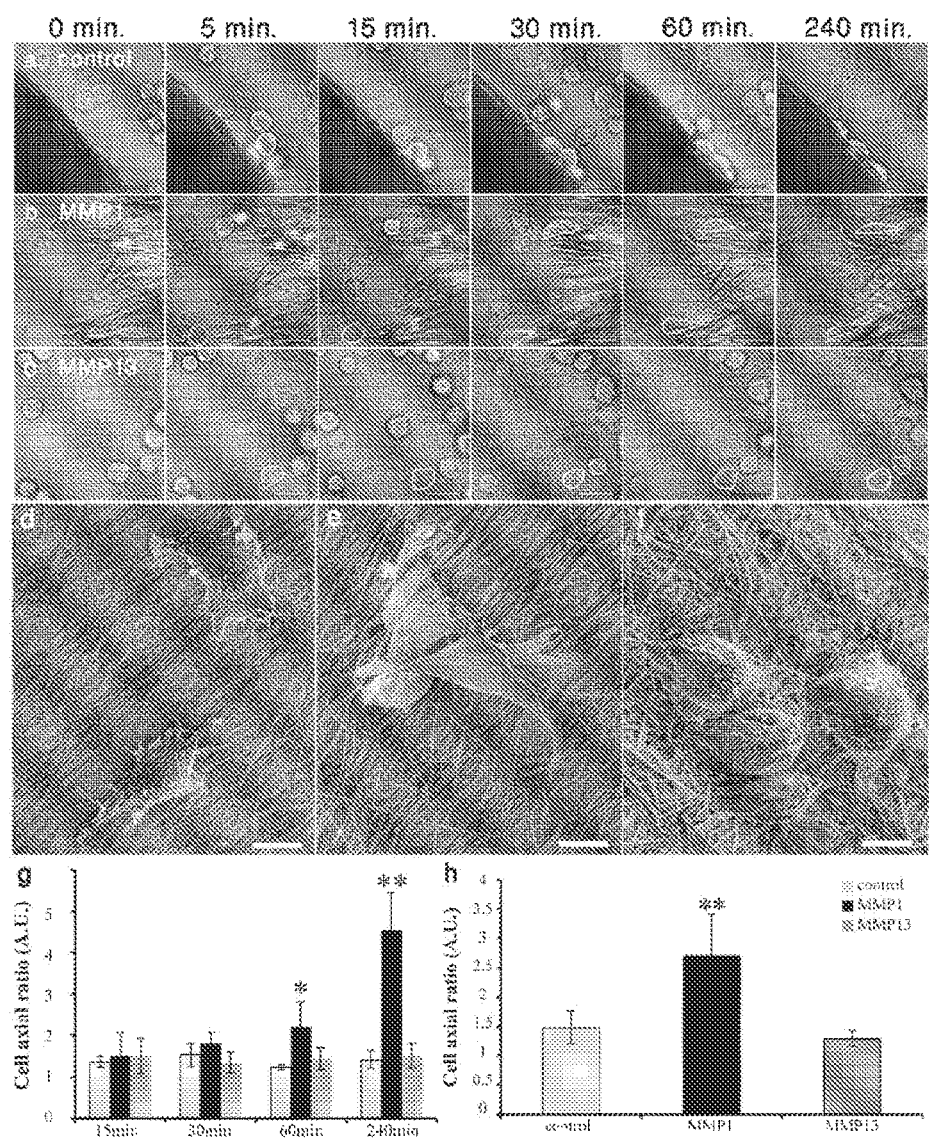
FIG. 7 shows cell-ECM interactions resolved by real-time in vivo imaging demonstrating the morphological features of the cells adhering close to (a) natural ECM or (b, c) ECM degraded by MMP-1 or MMP-13 at different time points after cell addition to the matrices. Colors specify the same cell under the same treatment at different time points (a,b,c) in order to follow the morphological changes. Scale bar=15 μm. SEM images of fibroblasts adhered to (d) natural ECM or (e, f) ECM degraded by MMP-1 or MMP-13. Scale bar=20 μm. (g) kinetics of cell axial ratios changes calculated from real-time in vivo imaging showing that cells adhered to natural or MMP-13-degraded ECM have an axial ratio of close to 1, in contrast to cells that adhered to MMP-1-degraded ECM which adopted elongated morphologies. (h) The velocity of cells moving on the glass coverslip towards natural ECM, or to ECM degraded by MMP-1 or MMP-13. Bars represent standard error. *p less than 0.05, **p less than 0.01.

Cell morphology and movement were characterized using real-time optical, and scanning electron microscopy (SEM). Whereas fibroblasts demonstrated movement towards native and MMP1-degraded ECM with similar velocity, in the presence of MMP-13-degraded ECM, they showed reduced or arrested motility (FIG. 7). Furthermore, cells adhering to, or within close proximity (less than 50 µm), to natural ECM demonstrated flattened morphologies. In contrast, cells interacting with MMP-1-degraded ECM exhibited elongated morphologies, and in the presence of MMP-13-degraded ECM the fibroblasts showed rounded contours and short extensions. The overall shape of cells was quantified by cell-axial ratio, to confirm the significant morphological differences in response to selective ECM remodeling (FIG. 7).

Figure 8:
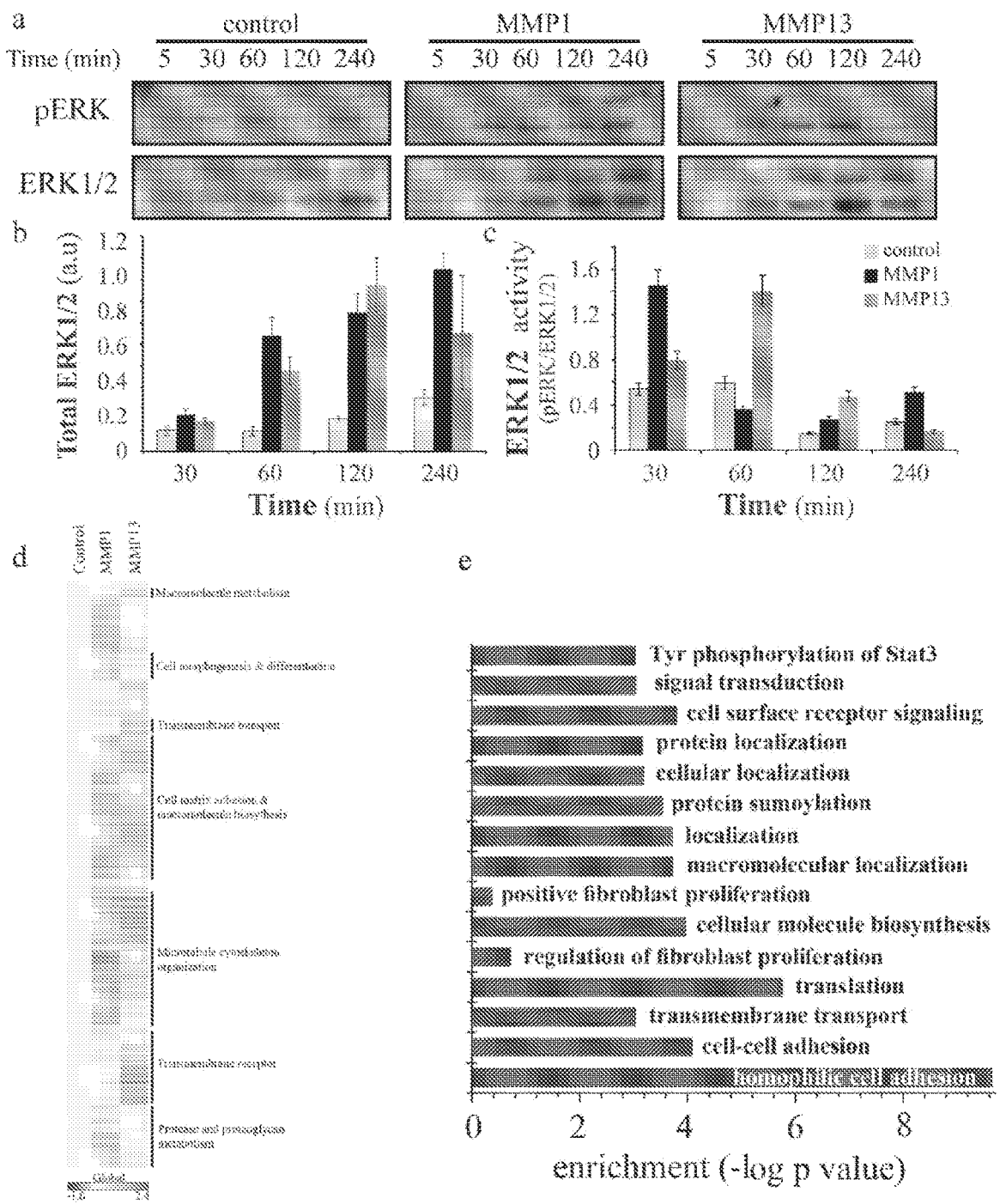
FIG. 8 shows cellular response to different ECM environments. (a) Western blot analysis demonstrates time-dependent ERK1/2 activation (pERK, top) and total protein presented as (general ERK1/2 (gERK, bottom) in rat-1 fibroblasts adhered to intact natural or degraded ECM. Time-dependent western blot quantifications of (b) gERK1/2 or (c) pERK ERK1/2 activity from lysates of rat-1 fibroblasts adhered to intact natural (blue), or ECM degraded by MMP-1 (red) or MMP-13 (black). (d) Differential gene-expression profile of ray-1 fibroblasts interacting with intact natural or degraded ECMs at two time points after cell seeding. Numbers specify different enrichment clusters: 1-cell-cell adhesion, 2-protein sumoylation, 3-positive regulation of purine metabolic process, 4-cell proliferation, morphogenesis, 5-sterol metabolic process. We applied a log2 transformation, floor to 3 and subtract each entry by the average of control sample genes. Top 5K changing genes were clustered by k-means (n=15). (e,f) Bar graphs representing qPCR analysis of specific validation of genes at 120 and 240 min post cell seeding. Error bars represent standard deviation from mean, *p less than 0.05, **p less than 0.01. (g) Functional Enrichment using GO annotation tool http://cbl-gorilla.cs.technion.ac.il/ database. Function and pathway enrichments were calculated using a Wilcoxon test p-value.
Figure 9:
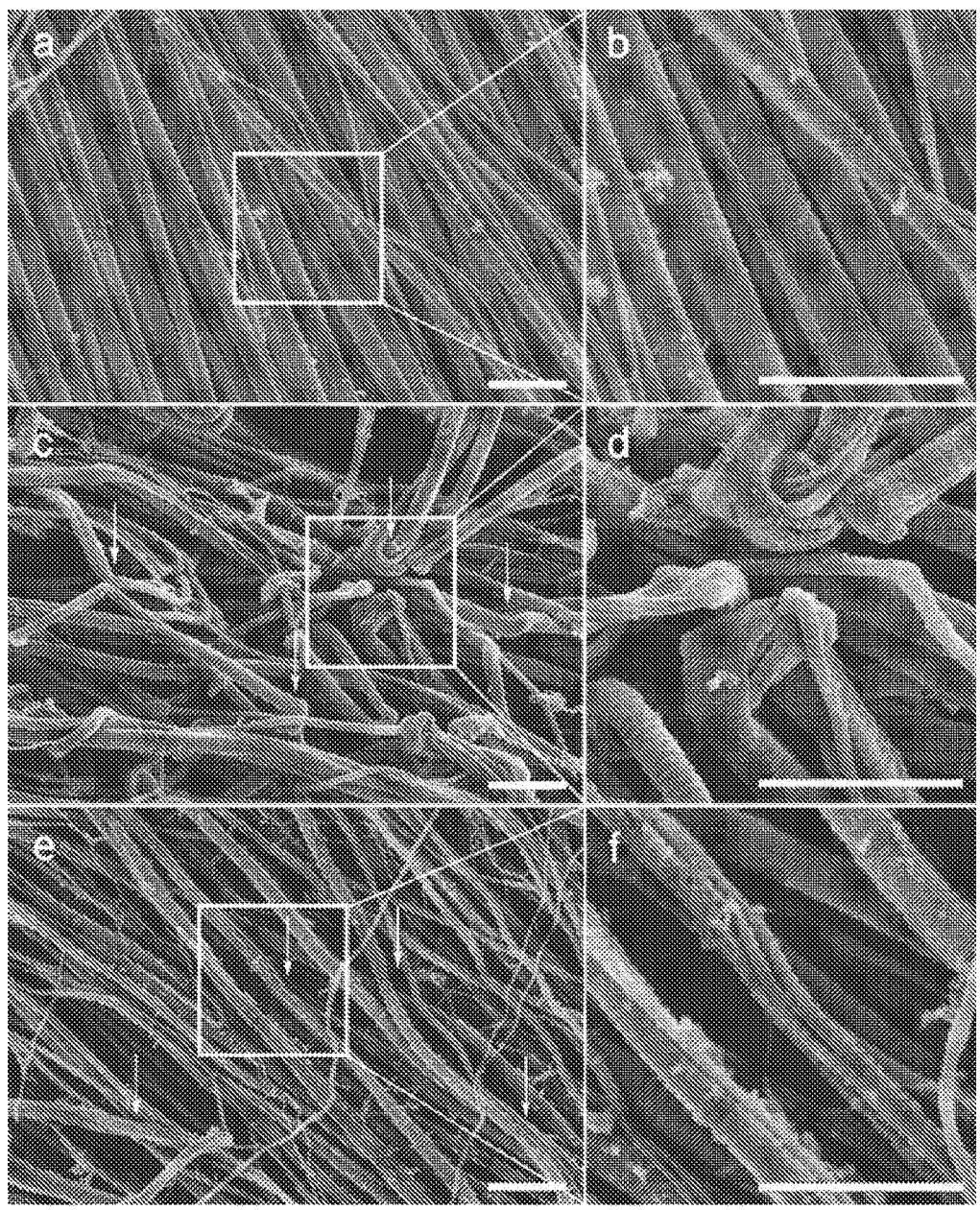
FIG. 9 shows SEM images of (a, b) natural ECM or (c, d) ECM degraded by MMP-1 or (e, f) MMP-13. The ECM degradation was done using 500 nM MMP1 or MMP13 at 30° C. for 24 h. Scale bar=1 μm.

Differential Remodeling of the ECM Drives Specific Activation of Intracellular Signaling Cascades and Gene Expression The differential phenotypes acquired by fibroblasts interacting with MMP-degraded ECM suggested that a typical and unique cellular response was transmitted by the ECM. Since cells regulate migration and proliferation mainly through the activation of extracellular signal-regulated kinase (ERK1/2) cascades, we examined the ECM-remodeling effects on this cellular cascade. Fibroblasts adhering to native ECM demonstrate a sustained mode of ERK1/2 activation; in contrast, a transient activation, peaking at 30 or 60 minutes, was detected in cells adhering to ECM degraded by either MMP-1 or MMP-13. Moreover, cells interacting with degraded ECM exhibited higher levels of total protein (represented as ERK1/2), indicating improved cell adhesion (FIG. 8a-c).

By profiling fibroblast transcriptional responses, we found 3163 genes that were differentially expressed in cells interacting with MMP-1- or MMP-13-remodeled ECM. The transcriptional responses showed significant enrichment in genes involved in cell adhesion, regulation of cell proliferation, and tissue morphogenesis (p less than or equal to $10^{-4}$). These genes take part in a broad spectrum of cellular pathways and reflect the dynamic fibroblast responses upon interaction with remodeled ECM as compared to non-treated controls. Specific genes involved in cell proliferation (Cdk9, Cdk14 and Cdk11b) were further amplified using qPCR, the analysis results of which supported the global gene expression data, further validating the induced proliferation in response to selective ECM remodeling (FIG. 8d-g). Furthermore, we demonstrated that changes occur in the gene expression levels of cell-cell and cell-ECM adhesion molecules such as protocadherins (Pcdhga2, Pcdhga10, Pcdhga9, Pcdhgb8 etc.), cadherins (N-cadherin (CDH2) and P-cadherin (CDH3)) and morphogenesis related genes (lama5, car9, Igf1r, Rhob, Tpm1).

Figure 18:
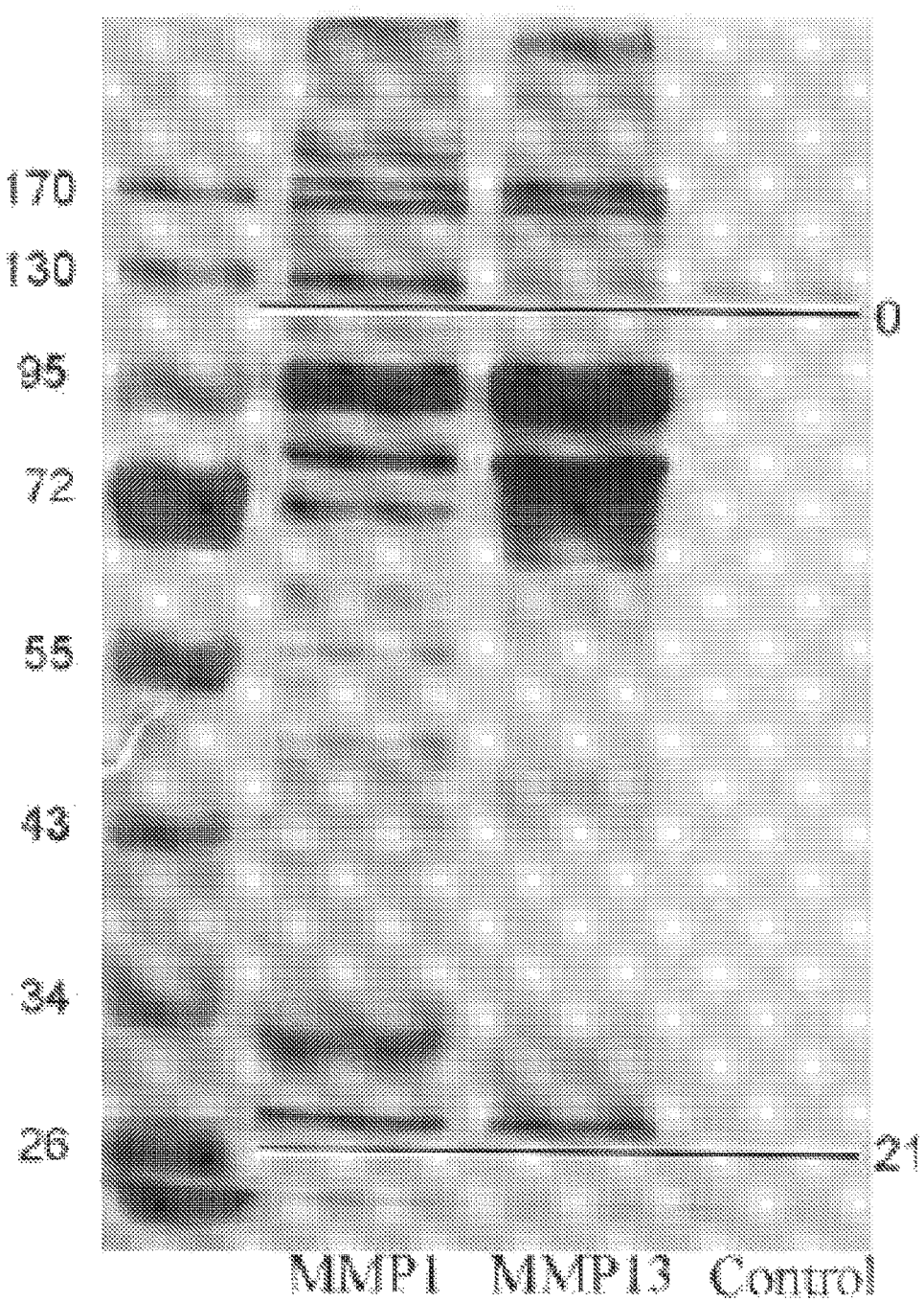
FIG. 18 shows a silver stained gel from decanted solutions post MMP degradation. Typical silver stained 1.5 mm SDS-PAGE gel electrophoresis patterns obtained from decanted solutions of control (untreated, incubated for 24 h at 30° C.) and treated (500 nM MMP-1 or MMP-13) fascicles after 24 h of incubation at 30° C. The gel reveals that in contrast to control the decanted solutions of MMP-1 and MMP-13-treated samples show multiple bands with molecular weights lower than 130 kDa, corresponding to degraded collagen fragments and/or other proteins. For MS analysis the 1.5 mm gels were used and 30 µL of samples were loaded. Lines 0 and 21 show the borders of gel, which was further used for MS analysis. These lanes were divided into 21 horizontal slices of 1.5 mm width, which were individually analyzed by nano-LC-ESI-MS/MS.

MMP-1 and MMP-13 Produce Distinct Micro-Scale Topographies and Visco-Elastic Alterations of ECM Since collagenases are highly potent proteases able to irreversibly cleave and re-shape the ECM landscape, we next focused on identifying the morphological changes exerted on the ECM as a result of specific collagenase activity. SEM images demonstrate that natural ECM consists mainly of collagen fibrils aligned along the fiber axis. Upon degradation by MMP-1 or MMP-13, the ECM's spatial organization is changed: the fibril alignment is disrupted, producing specific and robust digestion patterns. MMP-1 produces widely distributed broken and bent fibrils exhibiting multiple orientations, whereas MMP-13 caused the splitting of the native collagen fibrils into thinner ones as opposed to the straight and aligned intact fibrils (FIG. 18). The unique ECM-micro-scale topographies produced by MMP-1 and MMP-13 may lead to changes in ECM biomechanical properties on the macroscale level.

Figure 10:
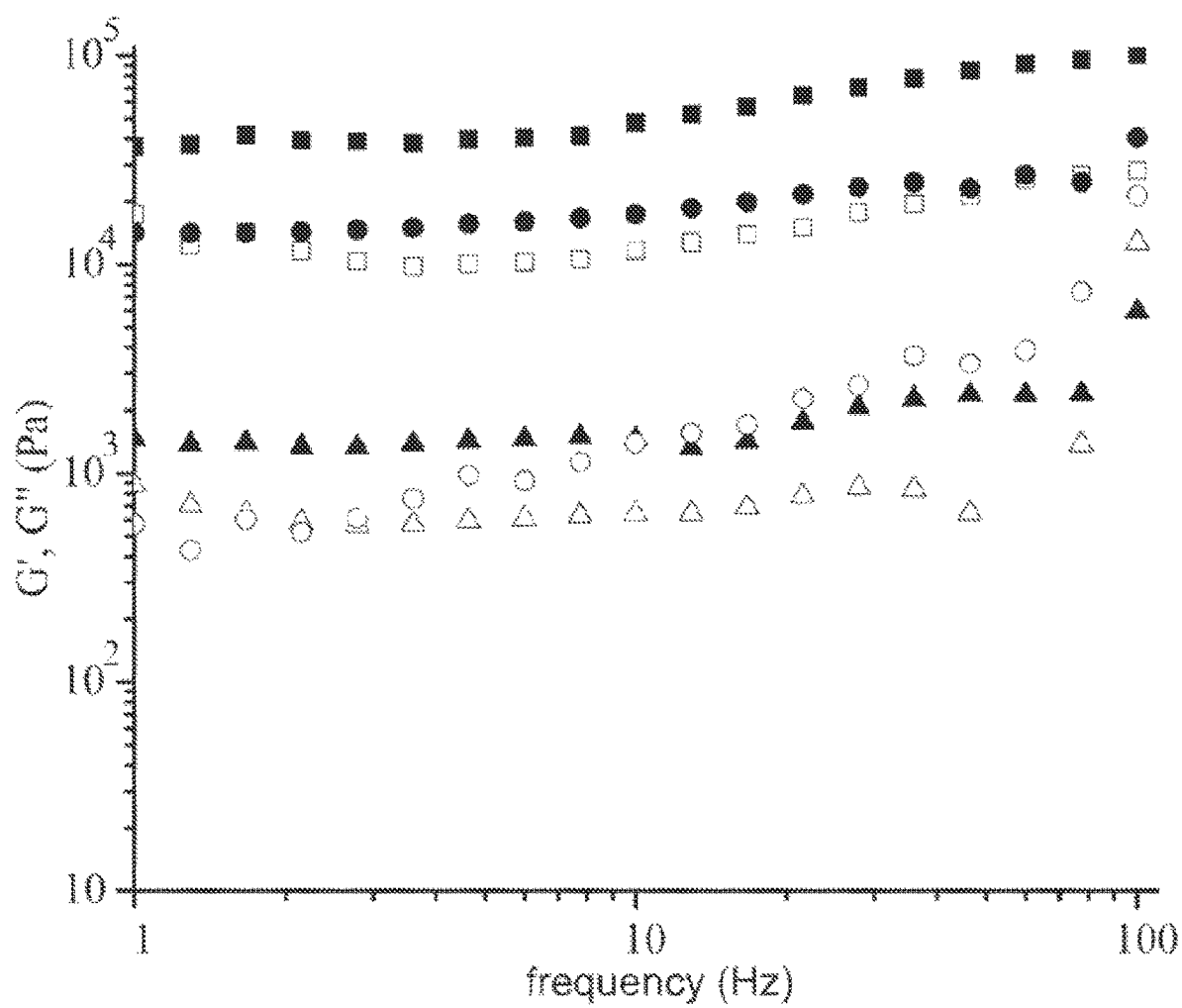
FIG. 10 shows the macro-rheological properties of intact and degraded ECMs. The frequency dependence of the averaged elastic G' (filled squares, triangles or circles) and viscous G" (empty squares, triangles or circles) moduli of intact or ECM degraded by MMP-1 or MMP-13, respectively.n Digested ECM samples were prepared by incubation of the fascicles in 500 nM MMP-1 or MMP-13 in TNC buffer at 30° C. for 24 h. The frequency varied from 1 to 100 Hz, measurements were made in triplicates.

By applying rheology we determined the frequency dependence of the elastic (G') and viscous (G") moduli, measuring the stress response of the ECM with frequencies varying from 1 to 100 Hz (FIG. 10). All samples exhibited gel-like behavior: G' was higher than G" and both parameters slightly increased with frequency. A comparative analysis of G' values points to intact ECM as being the stiffer (approximately 37 kPa) than degraded ECMs (G' of approximately 1.5 kPa for MMP-1 and approximately 14 kPa for MMP-13). In addition, the G" values revealed that intact ECM has the highest viscosity (approximately 1.75 kPa), whereas ECM altered by MMP-1 and MMP-13 is less viscous (G" approximately 0.6 kPa). Put together, we demonstrate that selective degradation results in distinct differences in the micro-scale topographies and visco-elastic properties of the ECM, which may lead to differential regulation of cell behavior.

Collagenolysis is Driven by Distinct Structural Mechanisms

We applied transmission electron microscopy (TEM) to visualize the degradation products present in decanted solutions after MMP digestion of native ECM. Such digested samples were either vitrified and observed by cryoTEM, or negatively stained. TEM images of native ECM decanted solutions revealed extremely low quantities of individual fibrils, with a characteristic banding pattern and axial periodicity of approximately 67 nm. The images display empty background areas around highly ordered fibrils, confirming the near-absence of degradation, as expected since Col I is very stable and abundantly crosslinked. (FIG. 11a, d, FIG. 12a, b).

Figure 11:
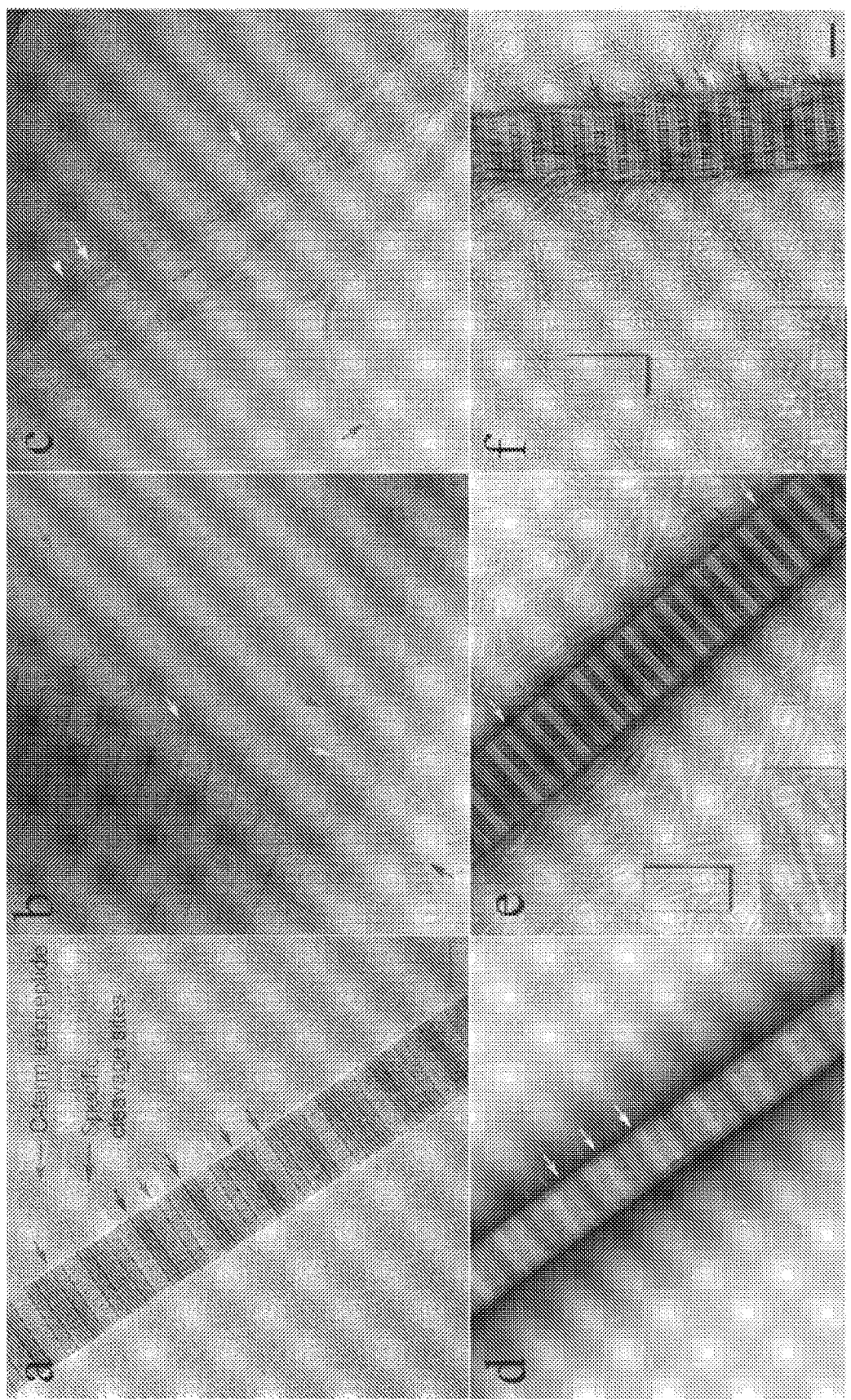
FIG. 11 shows TEM images of cryo-preserved and negatively-stained decanted solutions of (a, d) control samples, (b, e) samples treated with MMP-1 and (c, f) samples treated with MMP-13. All fibrils show banding pattern characteristic of Col I with an axial periodicity of approximately 67 nm. Arrows indicate Col I fibril polarity from C to N termini. Upper layer scale bar=100 nm; lower layer scale bar=200 nm.
Figure 12:
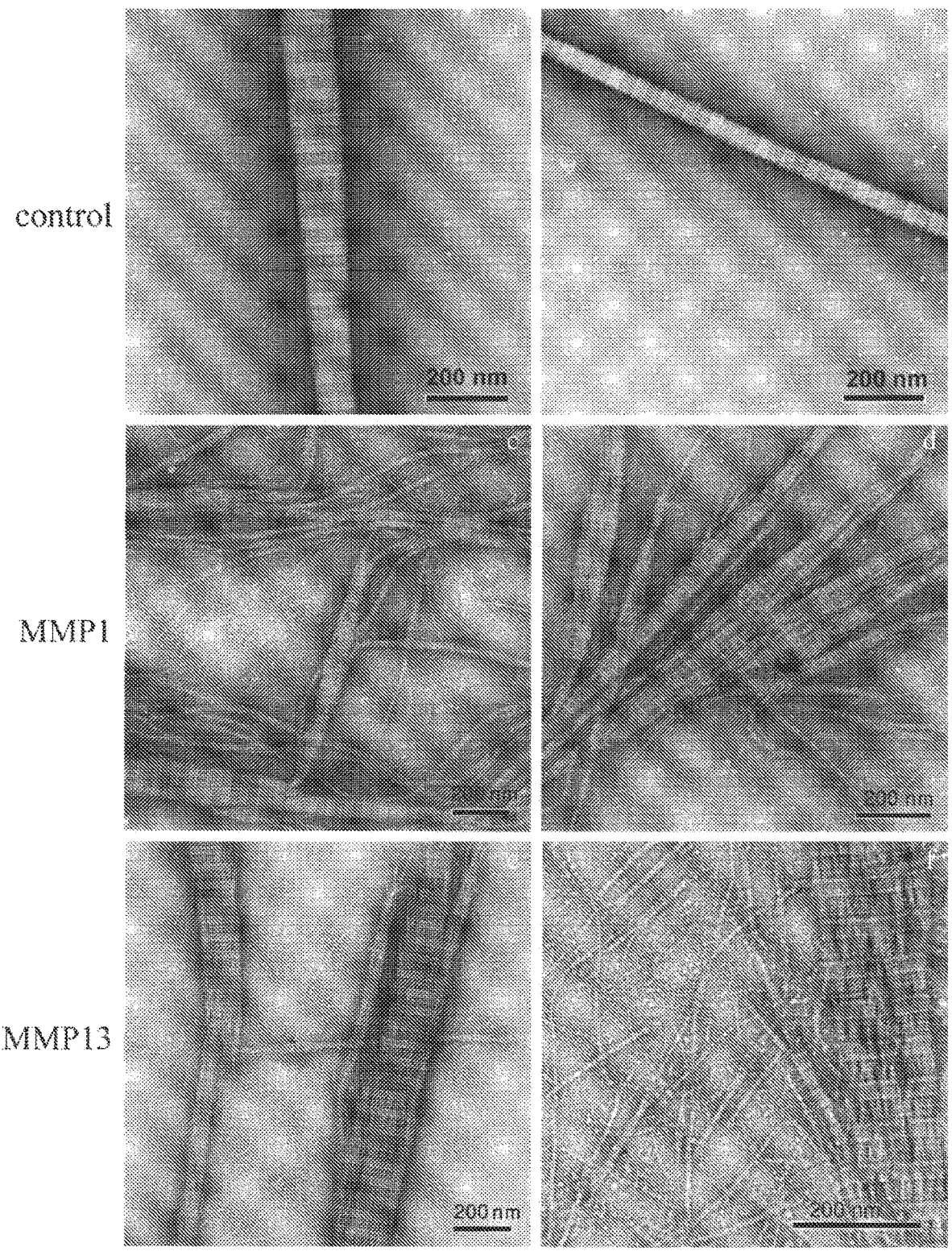
FIG. 12 shows representative TEM images of negatively stained Col I. (a, b) natural ECM was incubated at 30° C. for 24 h in the absence of collagenases. Only a few fibrils were detected in the decanted solutions. Col fibrils detected in decanted solutions of the specimens were incubated with (c, d) MMP-1 or (e, f) MMP-13.
Figure 13:
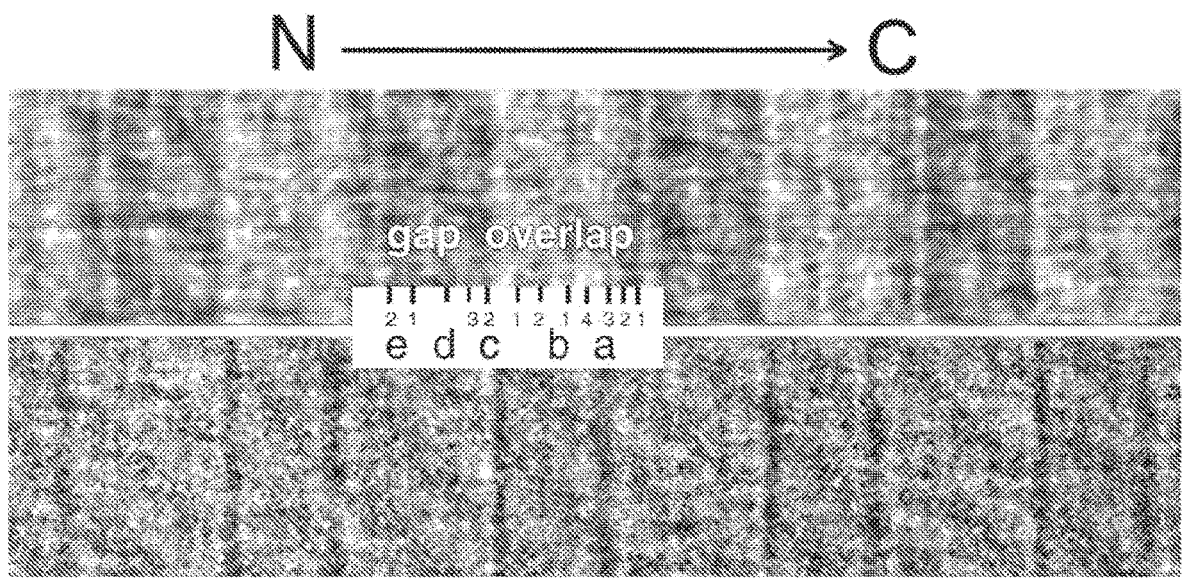
FIG. 13 representative TEM images of Col I bands. TEM imaging of Col I bands by negative stain (top panel) and cryoTEM (bottom panel). Alignment of the two allows the assignment of cryoTEM-imaged bands by the notation of Hodge & Schmitt. This led to the identification of the N- and C-telopeptide regions as well as others MMP cleavage sites on cryo-TEM images.

In contrast, samples treated with MMP-1 or MMP-13 display highly abundant, ruffled fibrils surrounded by unique degradation products, strongly suggesting that they are formed during MMP digestion (FIG. 11c, e, f, FIG. 12). The distinct "banding" observed in Col I fibrils has been used to correlate protein sequence location to the bands, and we correlated these assignments to the bands observed by cryoTEM (FIG. 13). This led to the identification of the N- and C-telopeptide regions as well as the site of MMP cleavage (FIG. 11).

Figure 14:
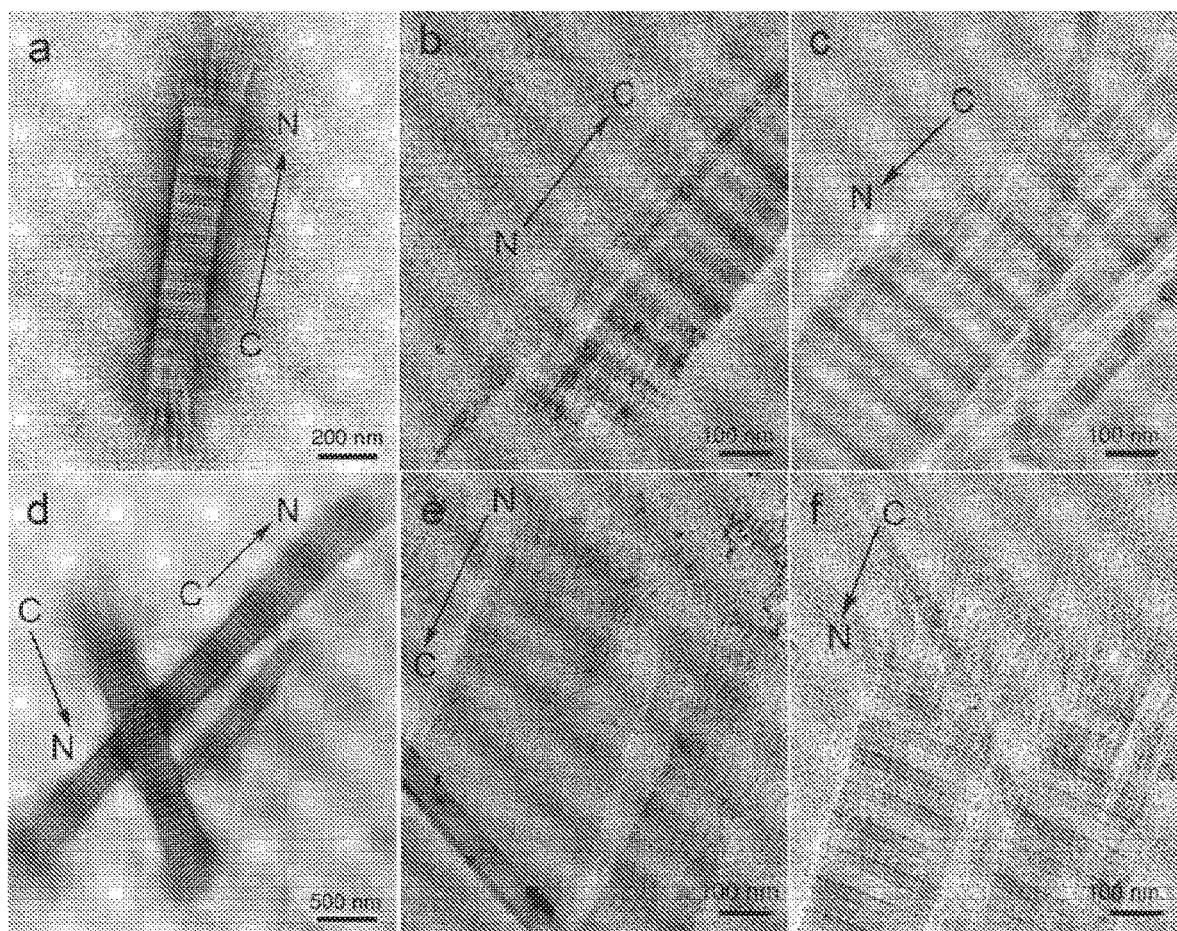
FIG. 14 shows TEM images of degraded Col I fibrils. TEM images of (a, d) negatively stained and (b, c, e, f) cryo-preserved Col I fibrils, formed during MMP-1 (a, b, c) or MMP-13 (d, e, f) processing. (a, d) show the digested fibrils as well as polarity of their ends. The anisotropicity of Col degradation by both MMPs may be detected by comparison of fibril termini, which display distinct morphologies. The N-terminal ends of the degraded fibrils are more compact than their C-terminal counterparts, suggesting that fibril degradation occurs mostly from the C- to the N-terminus of the fibril. CryoTEM images of (b, e) N-termini and (c, f) C-termini of the degraded fibrils.
Figure 15:
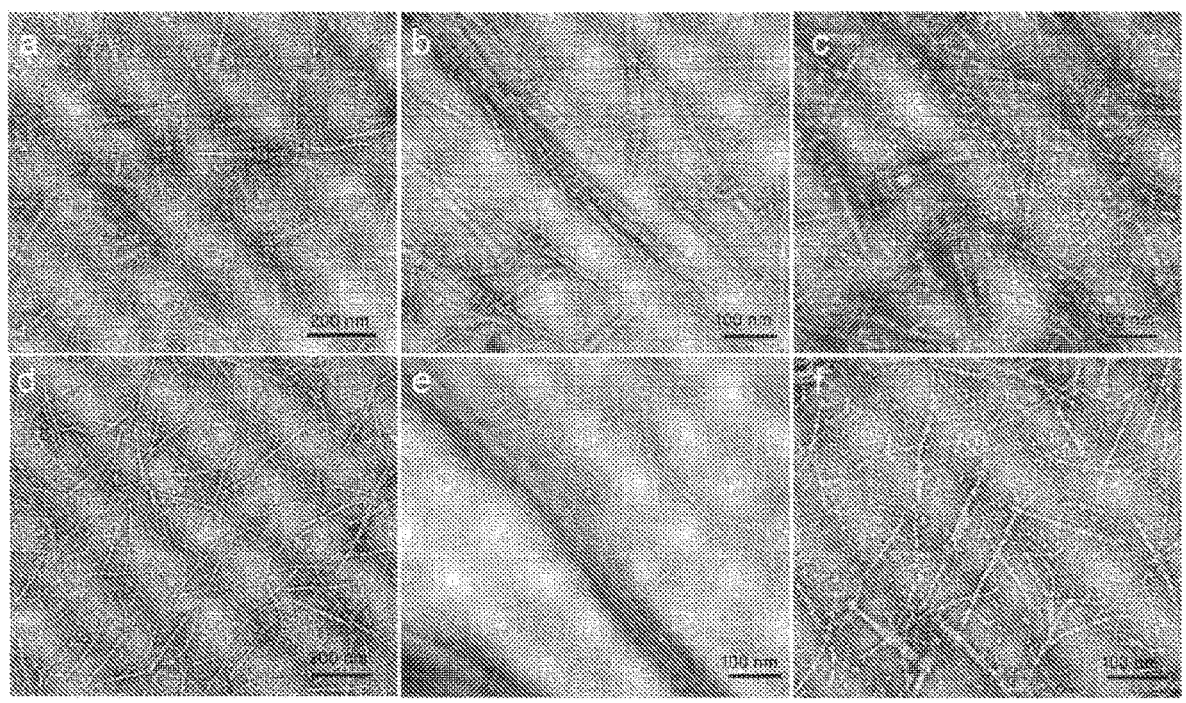
FIG. 15 shows TEM images of negatively stained degraded Col I fragments observed in decanted solutions of specimens treated by (a, b, c) MMP-1 or (d, e, f) MMP-13. The triangular morphologies predominate in the MMP-1-treated samples and rod-like fragments are prevalent in MMP13-treated samples.
Figure 16:
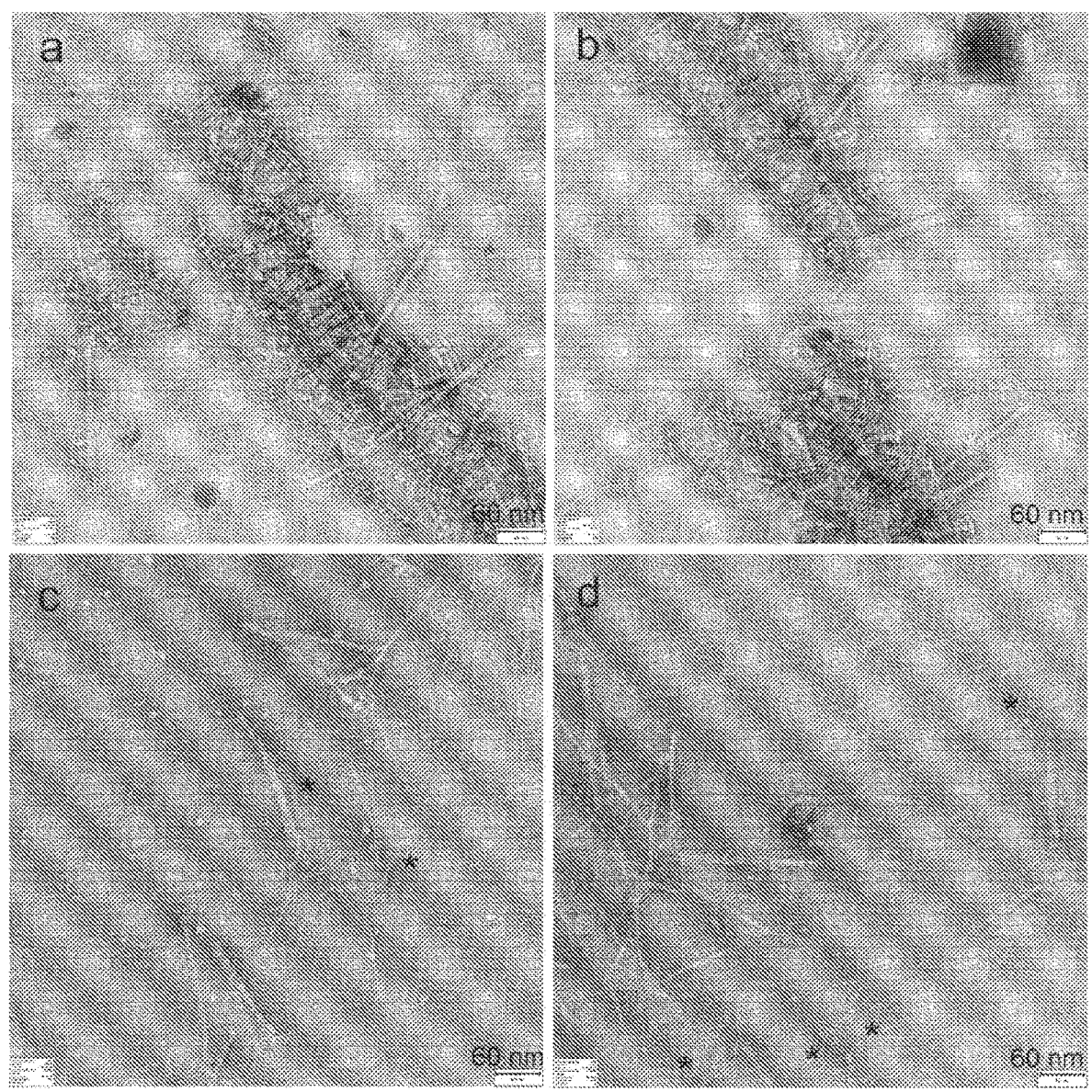
FIG. 16 shows small (¼) degraded Col I fragments visualized in decanted solutions using TEM. Degradation by (a, b) MMP-1 and (c, d) MMP-13. The small fragments (¼) degraded by MMP-13 are marked by stars. The images (a, b) further confirm that the C-termini telopeptides remained intact under MMP-1 proteolysis and degraded in the presence of MMP-13.
Figure 17:
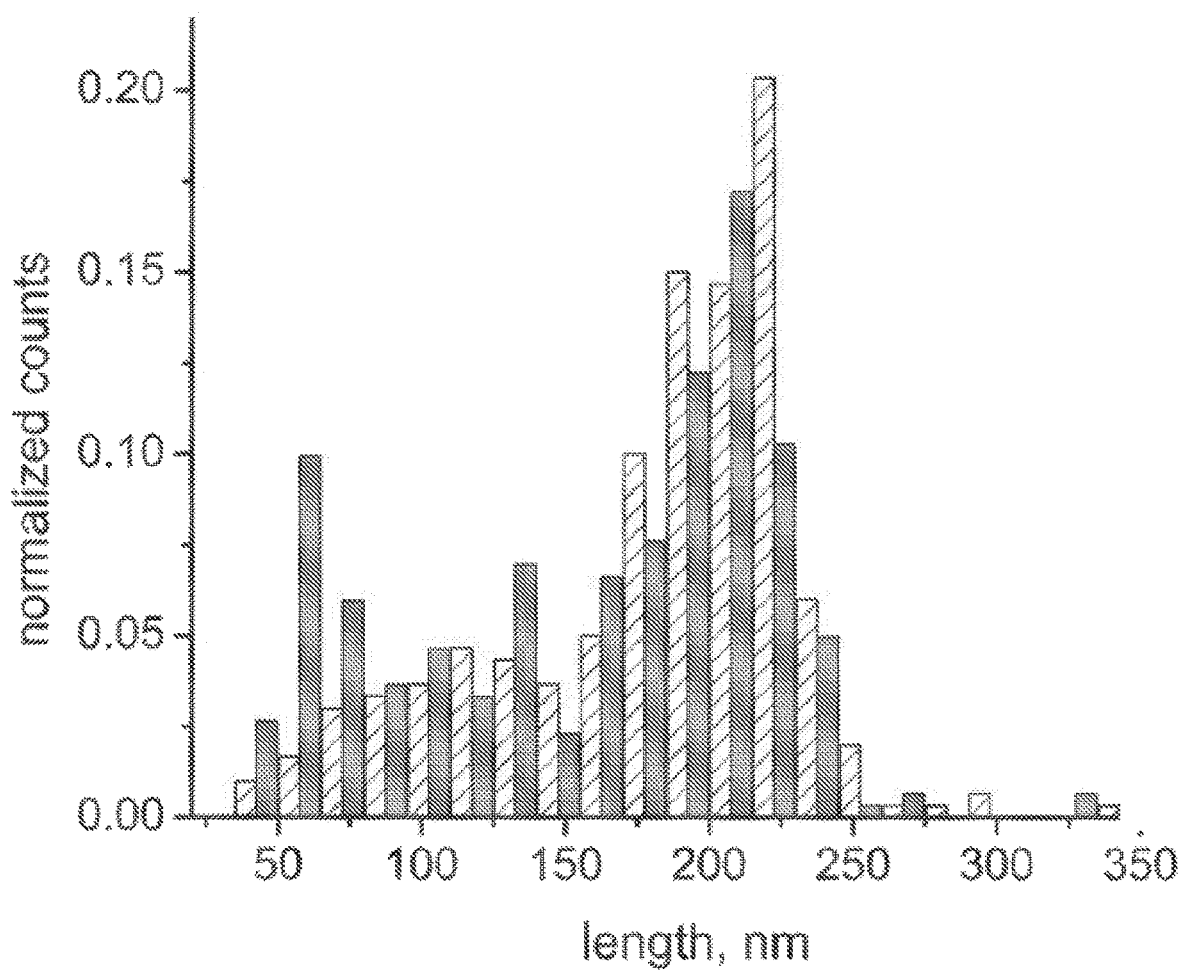
FIG. 17 shows statistical analysis of degradation products length. Histogram of normalized distribution of the lengths of Col I degraded fragments. The data show that both collagenases mainly digest Col I at the specific cleavage site corresponding to ¾ of monomeric length. The broadness of the Gaussian peaks indicates the existence of multiple cleavage sites in addition to the classical one (Gly791-Ile792 in $\alpha$1 and Gly784-Ile785 in $\alpha$2). 300 degradation products were measured for each collagenase in each measurement.

From these assignments, we observed structural anisotropicity of Col I cleavage in the cases of both proteases. The images reveal the "peeling" of degraded fragments, fringing off from the C- to N-terminus direction of the Col I fibrils (FIG. 11b, c, e, f). This directionality in MMP digestion may be dictated by the natural polarity of Col I fibrils, where collagen molecules align with C- and N-termini directed towards different poles of the fibrils. The anisotropicity of collagen degradation is also confirmed by comparison of fibril termini, which display distinct morphologies (FIG. 14). The N-terminal ends of the digested fibrils are more compact than their C-terminal counterparts, suggesting that fibril degradation occurs mostly from the C- to the N-terminus of the fibril. Most importantly, the cryoTEM images of digested fibrils show that cross-linked C-telopeptides are not digested during MMP1 processing, as gathered from their presence in the background of protealyzed morphologies extending out of the fibrils (FIG. 11b, arrows). In comparison, cross-linked C-telopeptides are not present in fibrils digested by MMP-13 (FIG. 11c), indicating the existence of a highly selective degradation mechanism in the Col I fibril. TEM images of negatively-stained samples reveal that both proteases produce heterogeneous populations of digested products, with triangular micro-fibril morphologies or rod-like fragments prevalent in MMP-1 or MMP-13-treated ECM, respectively (FIG. 11e, f, FIGS. 15-17). The normalized distribution of fragment lengths for MMP-1 and MMP-13 showed the highest abundances at 223±15 nm and 82±13 nm for MMP-1 and 207±15 nm and 83±15 nm for MMP-13 (FIG. 17), reflecting the signature cleavage position at ¾ and ¼ of collagen α-chains as well as other non-classical cleavage sites, marked by the broad Gaussian peak.

The individual rod-like fragments resulting from MMP13 digestion observed in the TEM images (FIG. 11f, FIG. 12, and FIG. 13) had a diameter of approximately 4 nm, corresponding to the proposed diameters of individual microfibrils (5-molecule bundle) from TEM and diffraction studies. We interpret the triangular morphologies present in MMP-1-digested samples to be formed by bundles of microfibrils that are connected at the C-telopeptide terminus Our observations strongly suggest that one microfibril is processed as a single cleavage incidence. This conclusion is supported by digestion kinetics studies showing a processive burst of 15±4 cleavage events occurring within one cut, corresponding to five triple-helical molecules in a microfibril (5×3=15 cleavage events).

Differential Proteomic Profiles are Generated During ECM Degradation

Mass spectrometry analysis (nano-LC-ESI-MS/MS) was used to examine the proteomic profiles of decanted solutions of ECM degraded either by MMP-1 or MMP-13. This analysis revealed distinctly different degradation patterns for MMP-1 and MMP-13, while as expected the control samples contained minimal amount of degradation products (FIG. 18). FIG. 19a,b shows matrisome proteins released from treated ECM, where Col I is the most abundantly degraded protein. The most striking differences between the two decanted solution profiles are the content and relative abundance of other ECM components such as proteoglycans, glycoproteins, ECM-affiliated proteins and other function-related ECM regulators. Thus, selective ECM degradation impacts not only ECM's morphology and visco-elastic properties but also its composition adding complexity to the observed combinatorial effect. Since trypsin digestion is highly specific, we correlated semi-tryptic peptides detected by MS with the proteolytic activity of MMPs, and determined Col I cleavage sites for MMP-1 and MMP-13 (FIG. 19c, FIG. 20). Interestingly, each MMP has its own unique cleavage sites (red), indicating distinct degradation patterns, which is supported by our TEM imaging observations.

Figure 19:
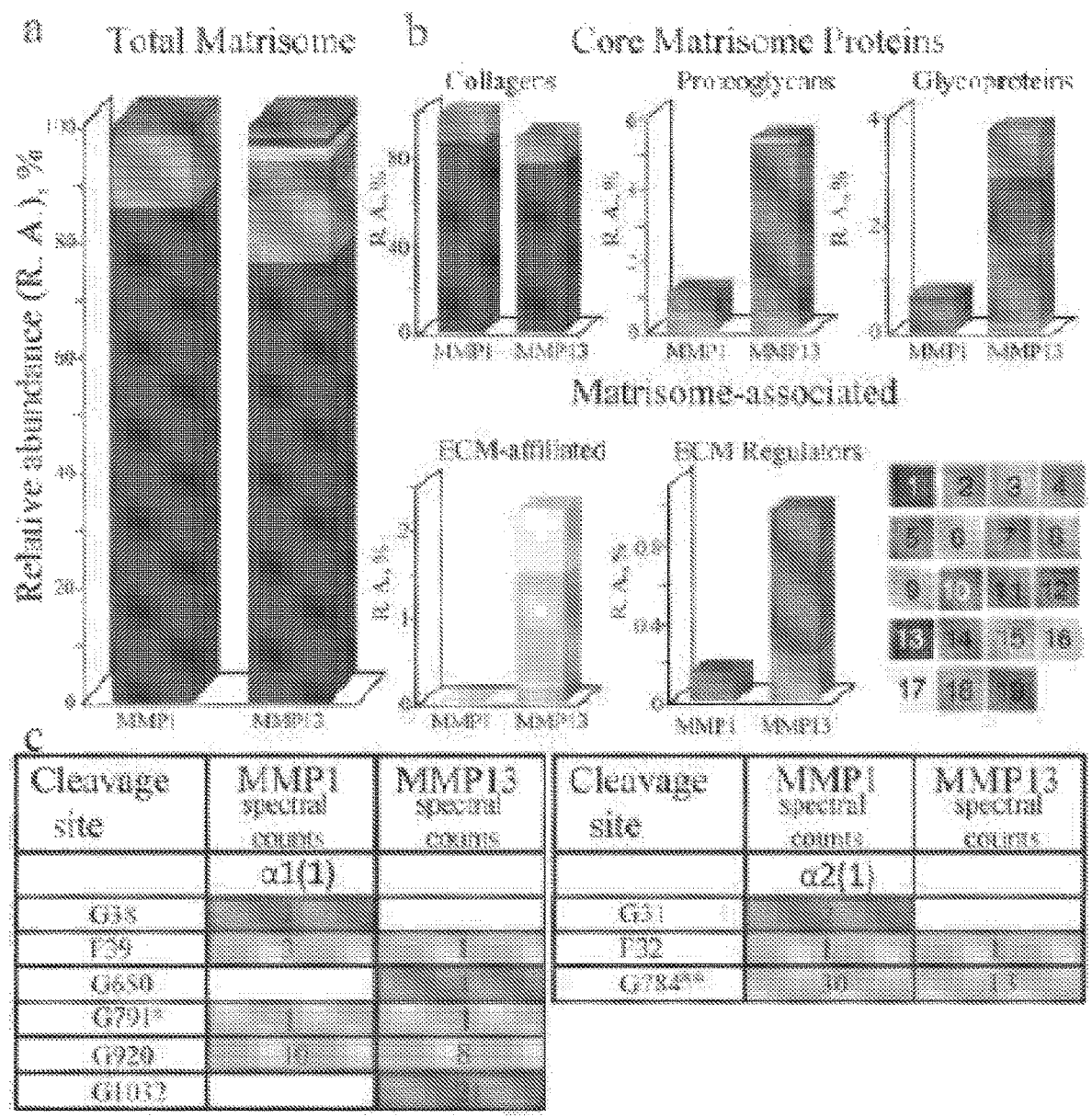
FIG. 19 shows mass spectrometry based proteomics data of ECM degraded by MMP-1 or MMP-13 determined from silver-stain SDS-PAGE and analyzed by nano-LC-ESI-MS/MS. (a) Relative abundances of matrisome proteins released during ECM degradation by MMP1 or MMP13. (b) Zoom-in of relative abundances of core- and matrisome-associated proteins. The identified proteins: 1-Col I, 2-collagen type VI, 3-collagen type XV, 4-decorin, 5-fibromodulin, 6-isoform 2 of aggrecan core protein, 7-proteoglycan 4, 8-fibulin 5, 9-tenascin-C, 10-transforming growth factor-β-induced protein ig-h3 precursor, 11-isoform long of hyaluronan and proteoglycan link protein, 12-lactadherin, 13-myocilin, 14-procollagen C-endopeptidase enhancer, 15-annexin A1, 16-isoform short of annexin A2, 17-annexin A5, 18-serine peptidase inhibitor clade F, member 1, 19-inter-α-trypsin inhibitor heavy chain H3. (c) Col I cleavage sites identified under proteolytic degradation by MMP1 or MMP13. Green: common for both MMP cleavage sites. Red: individual cleavage sites. *, **: specific cleavage sites. The absolute number of spectral counts identified for each Col I semi-tryptic peptide demonstrating differential efficiency of each MMP to any detected cleavage site (cleavage sites were reproducible in five experiments).
Figure 21:
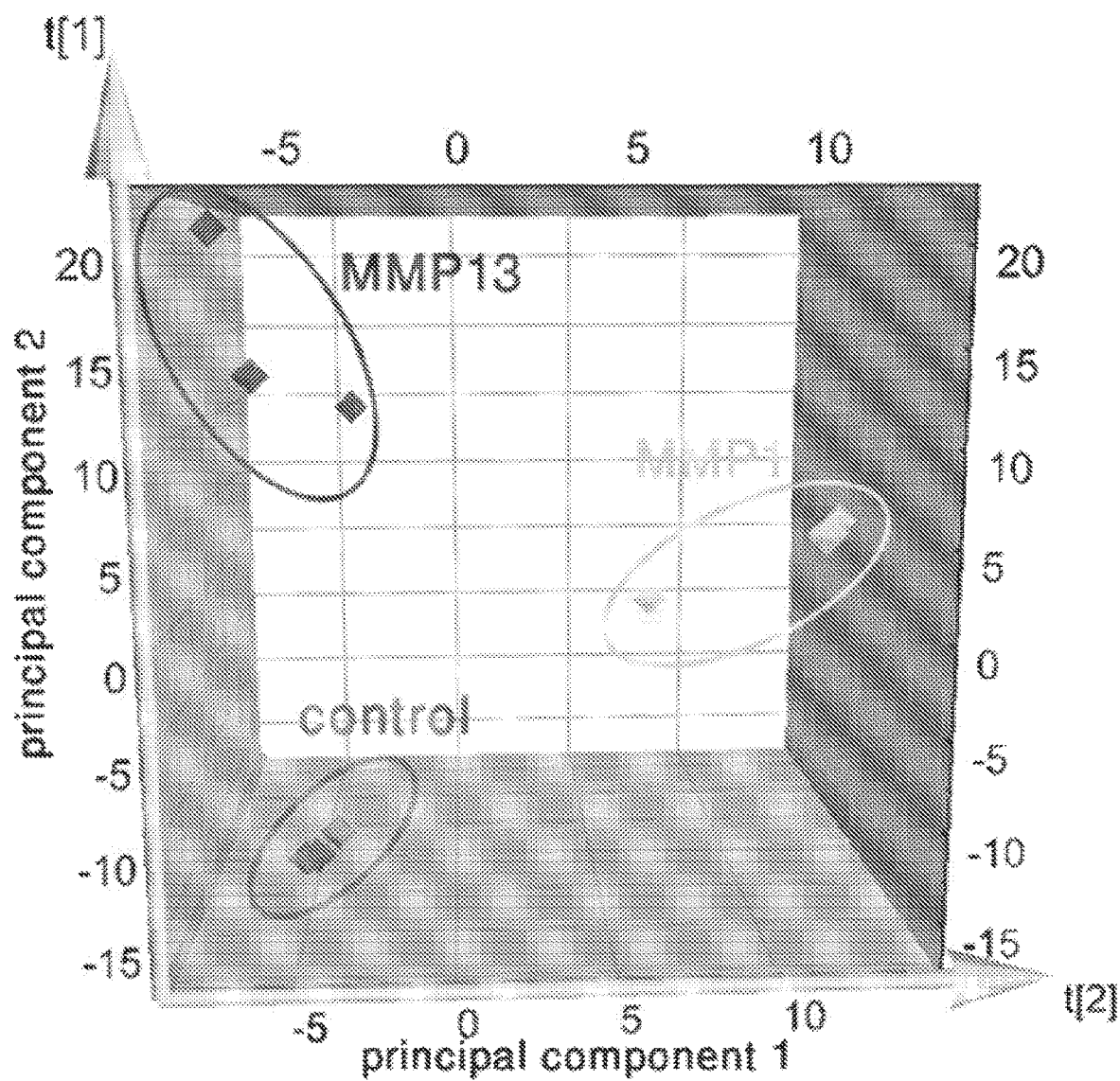
FIG. 21 shows a three-dimensional distribution of the principal component scores of mass spectra of Col I tryptic peptides detected from in-solution digestion. PCA shows the significant differences among mass spectra detected in decanted solutions of triplicates of three kinds of samples. The results show the close clustering of samples within each group, indicating low experimental variability within specific groups.

One remarkable observation is the detected degradation of C-telopeptide (Gly1032-Gly1033) only in the MMP-13-treated samples, confirming our TEM data. Additional principal component analysis (PCA) of Col I tryptic peptides resulted in three distinctly isolated, closely clustered populations (FIG. 21). This analysis further indicates that each collagenase degrades Col I fibrils using a distinct mechanism. Taken together, the data obtained demonstrate that both collagenases effectively degrade native collagen-rich ECM in a highly selective mode where MMP13 exhibits broader substrate specificity (FIGS. 19 and 20).

The constant remodeling of the ECM environment in healthy and diseased states creates a variety of stimuli to which cells are continuously subjected. There is a lack of understanding of the cellular responses to these stimuli. This study shows that ECM-cell crosstalk is governed by specific and selective activity of remodeling enzymes, that produce intricate combinatorial effects on the ECM, altering its topography, visco-elastic and biochemical properties. Our study used a wide variety of techniques that highlighted a range of distinct cellular and molecular responses to individual collagenase degradation. Although MMP-1 and MMP-13 are structurally homologous, and degrade Col I anisotropically, from the C- to N-terminus, we show that they have different specificity and selectivity to natural ECM, where MMP-13 exhibits broader substrate specificity than MMP-1 and produces a much greater number of matrisome degradation products.

In addition, we found that ECM degradation by either MMP-1 or MMP-13 reveals distinct collagen cleavage mechanisms, producing characteristic degradation fragments, as shown by both TEM images and MS analysis. The distribution analysis of Col I fragment lengths showed that each enzyme produced intra-population heterogeneity, confirming our MS data and indicating the existence of several cleavage sites on Col I. These significantly different cleavage patterns suggest that MMP-1 and MMP-13 access different epitopes of the assembled or partially digested collagen fibrils.

In addition, regions of helical instability and triple-helix local dissociation recently identified in native hydrated collagen fibrils may enable MMPs to access other exposed sites. Our data is further supported by PCA analysis demonstrating the distinct tryptic fragments of native MMP-1- and MMP-13-degraded Col I. Furthermore, TEM and nano-LC-ESI-MS/MS analyses provided proof that the C-telopeptides remain intact in MMP1-degraded ColI but are cleaved by MMP13.

Previous in vitro and in silico studies suggested that the cleavage of C-telopeptides is a critical initial step in collagenolysis, enabling the access of MMP to the cleavage site. Remarkably, our data show that collagenolysis can efficiently occur without prior C-telopeptide cleavage. Although the study's experimental conditions may not completely mimic the natural action of collagenases in vivo, using our simplified-natural ECM model we show that the degradation of collagenous and non-collagenous proteins, such as decorin, fibromodulin, aggrecan and proteoglycan 4, which are required for the proper organization of the ECM, also change the ECM's spatial organization and its nano-topography.

Finally, our results confirm that ECM degradation by both MMPs is accompanied by significant loss of mechanical rigidity on the macro-scale level. Both collagenases bring about ECM softening, where MMP-1 had a stronger effect than MMP-13. Softening of the ECM is known to reduce the spread of fibroblasts, decrease cell velocity and induce cell rounding. Remarkably, we observed these features in cells interacting with MMP-13-treated ECM but not in those interacting with MMP-1-treated. Thus, our data highlight that it is a combinatorial effect, one that includes the integration of all the events driven by MMP degradation that governs cell behavior.

We demonstrate that ECM degradation by MMPs improves the ability of fibroblasts to adhere to ECM, suggesting that ECM degradation leads to exposure of adhesion sites and/or signaling molecules bound to the ECM scaffold. Indeed, some of the genes that were induced in the cells following interaction with the degraded ECM were annotated as cell-adhesion molecules such as protocadherins (Pcdhga2, Pcdhga10, Pcdhga9, Pcdhgb8 etc.) belonging to the cadherin family. This family is known to interact with a wide range of binding partners regulating cell adhesion and activity. Furthermore, selective ECM degradation by collagenases altered ERK1/2-signaling cascade patterns, demonstrating that cells show increased proliferation tendencies following interaction with the degraded matrix. The transcriptional responses of fibroblasts interacting with intact or MMP-degraded ECM also support our finding that cells proliferation and adhesion are induced.

In conclusion, our results highlight the distinct roles of ECM remodeling enzymes in generating specific ECM properties, which affect cells and determine their fate. Our integrated experimental approach determined the specific combinatorial changes (topography, bio-mechanics, chemistry) that occur in the ECM during degradation reactions. Moreover, our approach reveals exquisite specificity and selectivity in the enzymatic activity of two structurally homologous collagenases in the context of their natural microenvironment. Given that tissues differ in their nature and morphology, we demonstrate the combinatorial events that generate tissue-specific ECM-cell dialogue. Collectively, our results highlight the importance of selective ECM-remodeling and pave the way for rationale specific protease therapeutic application.

Materials and Methods

Reagents and Antibodies: All analytical grade reagents were purchased from Sigma-Aldrich (Israel) unless otherwise mentioned. Purified deionized water was prepared using a Milli-Q water-purification system (Millipore, USA). Polyclonal anti-total ERK1/2 (cat. No M5670) and phosphorylated ERK1/2 (cat. No M8159) antibodies (Ab) were purchased from Sigma-Aldrich (Israel). Monoclonal MMP1 antibody was purchased from ThermoFischer Scientific (cat. No MA-515872). Monoclonal MMP13 antibody was purchased from Invitrogen (cat. No 701287). Cyclin D1 (cdk d1) antibody was purchased from Cells Signaling Technologies (cat. No 2922). Secondary antibodies (both anti Rabbit and mouse) conjugated to horseradish peroxidase (HRP) were purchased from Jackson ImmunoResearch (cat No.111-001-003 and 115-001-003 respectively).

Fascicle-Derived ECM Samples: Fascicle-derived ECM was prepared from adult Norwegian rat-tails (3-6 months). Specifically, rat-tails were dissected, tendon fascicles (ø~0.6 mm) were gently extracted and extensively washed in TNC buffer (50 mM TRIS, pH 7.4, 150 mM NaCl, 10 mM $CaCl_2$, 0.02% $NaN_3$) to remove the macroscopic debris of tissue and the excess proteases. The samples were then flash frozen and kept at −80° C. until processed. Digested ECM samples were prepared by incubation of the fascicles in 500 nM MMP1 or MMP13 in TNC buffer at 30° C. for 24 h. Reaction was stopped by the addition of 20 mM EDTA pH 8.0. The ECM samples were then gently washed with double deionized water with following washing (at least three times) in a suitable buffer.

Human MMP-1 Preparation: Briefly, the human proMMP1 was cloned in the pET3a expression vector. Bacteria were grown in LB Broth sterile medium (1 L containing 10 g Bacto-tryptone, 5 g yeast extract, 10 g NaCl, pH 7.5) with 150 µg/mL of ampicillin at 37° C. Protein expression was induced with 0.4 mM isopropyl-b-D-thiogalactoside at an OD600=0.6, and growth was allowed to continue for a further 4 h. Following expression, the enzyme accumulated in the fraction of inclusion bodies Importantly, all steps and refolding of proMMP1 were performed at 4° C. unless noted. The cells from 1 L of the culture (~16 g) were then harvested by centrifugation (3500×g, Sorvall LYNX4000 centrifuge, 15 min) and resuspended in 100 mL of lysis buffer (50 mM Tris, pH 8.5, 0.1M NaCl, 5 mM β-mercaptoethanol, 2 mM EDTA, 0.1% Brij-35 mM, containing 1 pill of Complete (EDTA-free) protease cocktail (Boehringer Mannheim). The cells were then passed through a hand homogenizer, and after addition of ~10 mg lysozyme, stirred for 10-20 min in cold room. The suspension was then sonicated (6 cycles of 10 sec and 20 sec off at 65% of Virsonic 60 power amplitude) and centrifuged at 27000×g (Sorvall LYNX4000) for 40 min. The pellet was further suspended in 100 mL of buffer containing 50 mM Tris, pH 8.0, 2 M NaCl, 5 mM β-mercaptoethanol, 2 mM EDTA, 0.1% Brij-35, 100 mM MgCl2) in the presence of 10-20 µL of 10 mg/mL of Dnase with 100 mM MgCl2, sonicated as described above until the sample lost its viscosity and collected as before. After the centrifugation at 27000×g for 40 min, the washing procedure was repeated and the pellet was suspended with 100 mL buffer containing 50 mM TRIS, pH 8.0, 5 mM β-mercaptoethanol, passed over hand homogenizer and centrifugation at 27000×g for 40 min. The pellet, containing inclusion bodies was then solubilized in 25 mL of denaturation buffer (50 mM Tris, pH 8.0, 20 mM DTT, 50 mM ZnCl2, 1 mM AHA, 8 M urea), stirred over night at room temperature and filtered through 0.2 µm. The urea-extract of protein was further purified on Hi-Trap monoQ (GE Healthcare) 5 mL column in FPLC ACTA, using a gradient of 500 mM NaCl/25 min concentration (buffer A: 6 M urea, 20 mM Tris, pH 8.0 and buffer B: 6 M urea, 20 mM Tris, pH 8.0, 1 M NaCl). Fractions containing MMP1 were diluted to 75 µg/mL at room temperature using buffer (20 mM Tris, pH 8.0, 20 mM cystamine, 6 M urea) and then dialyzed against 5-8 L of 50 mM Tris, pH 8.0, 2 mM AHA, 1 mM hydroxyethylsulfate, 4 M urea, 5 mM CaCl2, 0.1 mM ZnCl2, 300 mM NaCl, 5 mM β-mercapthethanol, 4 M Urea at 4° C. overnight under stirring. The next steps of refolding were done against 2 M Urea, 50 mM Tris pH 8.0, 10 mM CaCl2, 0.1 mM ZnCl2, 300 mM NaCl, 2 mM AHA overnight, under stirring at 4° C. and 50 mM Tris pH 8.0, 10 mM CaCl2, 0.1 mM ZnCl2, 300 mM NaCl, 2 mM AHA.

The renatured proteins were then filtrated through 0.2 µm, concentrated to approximately 10 mL by Amicon cell (Millipore) with 10MWCO PES membrane and purified by size-exclusion chromatography using Superdex 75 26/60 (GE Healthcare) pre-equilibrated with 50 mM TRIS pH 8.0, 300 mM NaCl, 10 mM CaCl2. The fraction eluted at 130-155 mL of SEC column was concentrated to approximately 3-5 µM and was stored at −80° C. in TNC with 10% glycerol.

Human MMP-13 Preparation: The human proMMP13 was cloned in the pCEP4 expression vector. HEK293 EBNA cells contain a pCEP4 expression plasmid with FLAG-proMMP13. The cells were initially grown on DMEM 10%

FCS with penicillin/streptomycin. Once the cells look alive and begun to divide, Geneticin (Sigma G418) was added to adjust the concentration of 250 µg/L (for EBNA-1 expressing cells). The cells were selected for Hygromycin B resistance medium containing 1000 µg/mL Hygromycin B. Once the cells grow well, they were passaged twice a week. When the cells were confluent in 15 cm dishes, the medium was replaced to DMEM, containing penicillin/strep and 0.2% LEH (lactalbumin enzymatic hydrolysate; basically amino acids, Sigma L9010). The medium was collected once a week and centrifuged to get rid of cell debris and was frozen at −20° C. The yield for Flag-tagged-proMMP13 from 1 L of medium is about 0.7 mg.

A hand-made 2-3 mL column with the resin flag was equilibrated with TNC buffer (50 mM TRIS pH 7.5, 150 mM NaCl, 10 mM $CaCl_2$) and collected medium was loaded with flow rate of 1-1.5 mL/min. The column was then washed by TNC buffer, followed by 50 mM TRIS pH 7.5, 1 M NaCl, 10 mM $CaCl_2$ and washed by TNC. The protein was eluted with 3×5 mL Hag peptide (0.2 mg/mL in TNC). Eluated solution was concentrated to 2-5 mL and loaded on Superdex 200 16/60 gel filtration column (GE Healthcare) in TNC buffer. The higher molecular weight peak shoulder on the main peak corresponds to proMMP13-TIMP1 complex. ProMMP13 is eluted at 72-75 mL of column volume and was stored at −80° C. in TNC with 10% glycerol.

Activation of proMMPs: MMP1 and MMP13 were activated with 1 mM APMA (4-aminophenylmercuric acetate) in TNC buffer (50 mM-TrisHCl pH 7.5, 150 mM NaCl, 10 mM CaCl2, 0.02% NaN3) at 37° C. for 60 min and enzymatic activity was tested.

Enzymatic Assay with Fluorogenic peptide: The enzymatic activity of MMP1 and MMP13 was measured at 37° C. by monitoring the hydrolysis of fluorogenic peptide Mca-Pro-Leu-Gly-Leu-Dpa-Ala-Arg-$NH_2$ at $\lambda ex=340$ nm and $\lambda em=390$ nm as previously described (3). The enzymatic reaction was initiated by addition of the different concentrations of fluorogenic peptide (0-100 µM). Fluorescence was recorded immediately and continuously for 30 min. Initial reaction rates were measured. And Vmax and $K_M$ were calculated. For MMP1 the Vmax=27±2 RFU/sec and Km 24.4±3.0 µM. For MMP13 Vmax=26±4 RFU/sec and Km 24.3±3.2 µM.

BCA Assay: To quantify and compare the amounts of degradation products released during ECM degradation reactions by MMP1 and MMP13 the decanted solutions were subjected to protein quantification with BCA protein assay kit (Abcam, ab102536). 600-800 µg/mL of total protein were detected in the decanted solutions of treated by MMPs samples in contrast to 0.03 µg/mL of controls.

Rat-1 Cell Culture: Rat-1 fibroblast cells were cultured in Dulbecco's modified Eagle's medium (DMEM) (Invitrogen) supplemented with 2 mM L-glutamine, 1% Penicillin/Streptomycin (Invitrogen) and 10% fetal bovine serum (FBS). Cells were maintained at 37° C. in a humidified atmosphere of 95% air and 5% $CO_2$. Rat-1 cells were detached with 0.25% trypsin/EDTA (Life Technologies.

Time-Lapse Video Microscopy: ECM samples (natural or degraded by MMPs) were prepared as described in paragraph 2 and the reaction was stopped by the addition of 20 mM EDTA. ECM were then gently washed with DDW and placed in a 8-well flat-bottom µ-slide (ibidi, GmbH). ECM samples were washed three times with a sterile PBS solution and twice with a DMEM medium. Rat-1 fibroblasts (1.5×10$^5$ cells/mL) were then seeded to the wells with degraded and natural ECM in a serum starved, phenol free medium (Dulbecco's modified Eagle's medium (DMEM) supplemented with 2 mM L-glutamine, 1% Penicillin/Streptomycin and 0.1% fetal bovine serum). Each slide was then placed in the stage incubator on a DeltaVision® Core microscope with phase-contrast optics at a magnification of ×60 at 37° C. and 5% $CO_2$. Images were captured with a CoolSNAP HQ2 CCD camera every 5 min during periods of up to 4 h. Data acquisition and movie assembly were performed using softWoRx for Linux; movies were imported into Quicktime format (version 10.0, Apple computers) for further analysis using Photoshop CS4 (Adobe, Calif., USA). Cell velocities and cell axial-ratio were quantified using ImageJ (p value<0.05, student t-test).

Scanning Electron Microscopy: ECM samples of 1 cm length were prepared as described in section 2 and washed as described in section 5. Rat-1 fibroblasts (1.5×10$^4$ cells/mL) were seeded in their growing medium to each well of a Corning flat-bottom 24-well culture plate containing coverslips with natural and degraded ECM samples, and incubated for 4 h at 37° C. and 5% $CO_2$. At the end of the incubation period, samples were fixed in a 0.1 M cacodylate buffer (pH 7.4) solution containing 2.5% paraformaldehyde and 2.5% glutaraldehyde, pH 7.2, for 30 min at RT and washed three times by the same buffer. The cells were postfixed in 1% osmium tetroxide in the cacodylate buffer for 1 h and washed with three changes of the buffer. The samples were then stained with 4% sodium silicotungstate (pH 7.0) for 45 min and dehydrated through an ascending series of ethanols ending in 100% ethanol. Next, the samples were dried in a critical point dryer and gold-sputtered for imaging. In order to observe ECM topographies, the process of postfixation with osmium tetroxide was excluded. The samples were observed in a Zeiss FEG Ultra55 SEM operating at 2 kV. Image brightness and contrast levels were adjusted using Photoshop CS4 (Adobe, Calif., USA). Cell axial ratios were quantified using ImageJ (p value<0.05, t-test).

Cell Lysis and Western Blotting: ECM samples of 1 cm length were prepared as described in section 2 and 5. Rat-1 fibroblasts were grown as described in section 4, and serum starved prior further analysis (0.1% FBS, 16 h). Cells were seeded (7.5×10$^4$ cells/mL) onto natural or degraded ECM samples placed in a Corning flat-bottom 24-well culture plate and incubated for 5, 30, 60, 120, 240 min at 37° C. and 5% $CO_2$, in a serum starved medium (Dulbecco's modified Eagle's medium (DMEM) supplemented with 2 mM L-glutamine, 1% Penicillin/Streptomycin and 0.1% fetal bovine serum). At the end of incubation period, the ECM samples were carefully removed washed in PBS buffer then incubated in RIPA buffer (20 mM Tris, pH 7.4, 137 mM NaCl, 10% glycerol, 1% Triton X-100, 0.5% deoxycholate, 0.1% SDS, 2 mM EDTA, 1 mM PMSF) to produce cell lysates. Using this procedure we could isolate cell population that directly adhered to natural or degraded ECM. Cell lysates were then analyzed by Western blot analysis using the indicated antibodies. Each experiment was performed three times in duplicates to test for reproducibility and to obtain statistically significant data. Quantifications of western blot experiments were performed using ImageJ. Blots were scanned and band densities were measured and quantified. ERK1/2 total amount was measured based on band intensities then pERK band intensities were measured. The calculated ERK1/2 activity is measured as a relation of pERK to ERK1/2 total amount (pERK/ERK1/2).

Differential Gene Expression Analysis: Sample preparation. The wells of flat-bottom 96 Nane plates were completely covered with ECM. Collagenases were added to the wells and the degraded ECMs were prepared as described in paragraph 2. At the end of the degradation reaction all wells were washed as described in paragraphs 2 and 5. Rat-1 fibroblasts were seeded (2.5×10⁴ cells per well) in duplicates and incubated for 2 and 4 h at 37° C. and 5% CO2. The cells adhered to ECM were sent for whole-genome mRNA profiling.

RNA isolation. For RNA isolation, cells adhered to native or degraded ECM were directly lysed in the presence of QIAzol and total RNA was extracted with the miRNeasy Mini Kit (Qiagen). The RNA integrity number (RIN) was determined using the TapeStation System (Agilent Technologies). Quantity of RNA was determined by Qubit Fluorometric Quantitation kit (Life Technologies).

Preparation of RNA sequencing libraries. For RNA-Seq libraries preparation, total RNA was fragmented into average size of 300 nucleotides by chemical heat (95° C.) treatment for 4.5 min (NEBNext Magnesium RNA Fragmentation Module). The 3' polyadenylated fragments were enriched by selection on poly dT beads (Dynabeads Invitrogen). Strand-specific cDNA was synthesized using a poly T-VN oligo (18 T) and Affinity Script RT enzyme (Agilent). Double-strand DNA was obtained using Second strand synthesis kit (NEB). DNA ends were repaired using T4 polynucleotide kinase and T4 polymerase (NEB-Next). After the addition of an adenine base residue to the 5' end using Klenow enzyme (NEB-Next), a barcode Illumina compatible adaptor (IDT) was ligated to each fragment. The washed DNA fragment was amplified by PCR (12 cycles) using specific primers (IDT) to the ligated adaptors. The quality of each library was analyzed by TapeStation (Agilent).

Pre-processing of RNA-Seq data. All reads were aligned to the rat reference genome (Rat RN5) using the TopHat aligner (5). The raw expression levels of the genes were calculated using the ESAT program (http://garberlab.umassmed.edu/software/esat/). ESAT takes as input a transcriptome annotation set (we used RefSeq annotations downloaded from the UCSC genome browser), and uses a scanning window approach to assign the most enriched peak to each annotation. This is done for every isoform, and the ends are collapsed for the genes. We use the collapsed gene counts for our analysis. Based on the principles of the protocol, raw read counts can be used directly for gene expression, as gene length bias is eliminated when sequencing fixed-length fragments at the gene end. Normalization was done using DESeq based on the negative binomial distribution and a local regression model. For the data table used for heat map, we applied a log2 transformation, floor to 3 and subtract each entry by the average of control sample genes. Top 5K changing genes were clustered by k-means (n=15). Significant change was considered as more than 50%.

Enrichment analysis of biological functions and pathways. For pathways and functional analysis we compared cellular pathways using http://cbl-gorilla.cs.technion.ac.il/database. Function and pathway enrichments in a profile were calculated using a Wilcoxon test P-value.

qPCR run and analysis. RNA was isolated from cultured cells using the miRNeasy extraction kit (Qiagen) according to the manufacturer's instructions. cDNA was obtained with cDNA Reverse Transcription Kit (Applied Biosystems). qPCR was performed using an ABI 7300 instrument (Applied Biosystems). Values were normalized to GAPDH control. Each RNA sample was run in triplicate, and results are a mean of two-three separate runs. Statistical analysis and data presentation: Data is presented as mean fold changes using the $2^{-\Delta\Delta CT}$ method on the mean of all six measurements (two runs in triplicates). Namely, the height of columns on graph correspond to the $2^{-\Delta\Delta CT}$. Standard deviation of the mean (s.d) was calculated for original ΔCT data. Results were statistically analyzed on original data using student t-test in Microsoft Office Excel or Prism.

Transmission Electron Microscopy: Sample preparation. The samples were prepared and reactions were stopped as described above. Since fascicles did not degrade in the absence of MMPs, there were no individual fibrils in the untreated by collagenases samples. For obtaining individual fibrils in control samples, the collagen fibrils were gently dissected from fascicles prior the incubation. The fascicles were kept hydrated. The observed under such preparation fibrils were used as controls.

Cryo-TEM microscopy. Decanted solutions from degradation experiments (5 μL) were applied to glow-discharged copper TEM grids coated with lacey carbon (SPI Supplies, West Chester, Pa., USA). The samples were blotted and plunged into liquid ethane using a Leica EM-GP automated plunger. Grids were stored in liquid nitrogen and the images were taken in a low-dose mode at −178° C. using a Gatan 626 cryoholder, on a Tecnai T12 electron microscope at 120 kV, or on a Tecnai F20 microscope at 200 kV. Images were recorded on either a TVIPS F224 camera or a Gatan US4000 camera. Images were band-passed filtered for figure preparation.

Negative staining. Decanted solutions from degradation experiments (5 μL) were deposited on glow-discharged, carbon-coated grids and stained with 4% sodium silicotungstate (pH 7.0) for 30 s. The samples were then observed with a Tecnai T12 TEM (FEI, Eindhoven, The Netherlands) operated at 120 kV. Images were recorded with a MegaView III CCD camera (SIS, Muenster, Germany), or a Tietz TVIPS F224 camera.

Proteomic Analysis by LC-MS/MS: Two approaches were taken to analyze degraded Col I ECM. In the first approach, the decanted solutions, were first separated by SDS-PAGE, then the lanes with the bands of degraded products were cut into 21 lines, and each of 21 lines was subjected to in-gel tryptic digestion followed by LC-MS/MS analysis. In the second approach, samples were subjected to in-solution digestion and ion-intensity based label-free quantification. The mass spectrometry proteomics data have been deposited to the ProteomeXchange Consortium via the PRIDE partner repository with the dataset identifier PXD003553.

ECM preparation. The fascicles were prepared and treated by MMPs as described in paragraph 2. The decanted solutions were used for MS-based proteomics. The total amount of degraded products was determined by BCA assay.

SDS-PAGE gels. For Silver stained gels 5 uL of sample reduced buffer (×4) were immediately added to 15 uL of the decanted solutions containing 20 mM EDTA and boiled for 3 min at 90° C. The samples were then loaded on a 12% gel of 0.7 mm thick. For Coomassie Stained gels 30 uL of samples prepared exactly as described for silver stained gels, were loaded on the 12% gel of 1.5 mm thick. PageRuler unstained protein ladder (Fermentas International Inc.) was used as molecular weight standards. Protein bands from Silver Stain gel (21 slices, 1.5 mm high, or 1 cm lane from Commassie Stain gel (Figures not shown) were excised from gel and destained using multiple washings with 50% acetonitrile in 50 mM ammonium bicarbonate. The protein bands were subsequently reduced, alkylated and in-gel digested with bovine trypsin (sequencing grade, Roche Diagnostics, Germany), at a concentration of 12.5 ng/μL in 50 mM ammonium bicarbonate at 37° C., as described. The peptide mixtures were extracted with 80% CH3CN, 1% CF3COOH, and the organic solvent was evaporated in a vacuum centrifuge. The resulting peptide mixtures were reconstituted in 80% Formic Acid and immediately diluted 1:10 with Milli-Q water prior to the analysis by online reversed-phase nano-LC (liquid chromatography)—electrospray ionization (ESI) tandem mass spectrometric analyses (MS/MS).

MS from solutions Immediately after stopping the enzymatic reaction, the decanted solutions were transformed into separate tubes and brought for MS analysis. The total protein concentration of the samples was adjusted such that the same protein amount was analyzed by LC-MS/MS for all samples. Proteins were first reduced using dithiothreitol (Sigma Aldrich) to a final concentration of 5 mM and incubated for 30 min at 60° C. followed by alkylation with 10 mM iodoacetemide (Sigma Aldrich) in the dark for 30 min at 21° C. Proteins were then digested using trypsin (Promega, Madison, Wis., USA) at a ratio of 1:50 (w/w trypsin/protein) for 16 h at 37° C. Digestions were stopped by addition of formic acid to a concentration of 1%. The samples were stored at −80° C. in aliquots.

Nano-LC-ESI-MS/MS of in-gel digested samples. Peptide mixtures were separated by online reversed-phase nanoscale capillary LC and analyzed by ESI-MS/MS. For the LC-MS/MS, the samples were injected onto an in-house made 15 cm reversed phase spraying fused-silica capillary column (inner diameter 75 µm, packed with 3 µm ReproSil-Pur C18A18 media (Dr. Maisch GmbH, Ammerbuch-Entringen, Germany), using an UltiMate 3000 Capillary/nano LC System, consisting of Famos™ Micro Autosampler, Switchos™ Micro Column Switching Module (LC Packings, Dionex). The flow rate through the column was 250 nL/min. An ACN gradient was employed with a mobile phase containing 0.1% and 0.2% formic acid in Milli-Q water in buffers A and B, respectively. The injection volume was 5 µL. The peptides were separated with 50 min gradients from 5 to 65% ACN. The LC setup was connected to the LTQ Orbitrap mass spectrometer (Thermo Fisher Scientific, Bremen, Germany) equipped with a nano-electrospray ion source (Thermo Fisher Scientific, Bremen, Germany) In the nano-electrospray ionization source, the end of the capillary from the nano-LC column was connected to the emitter with pico-tip silica tubing, i.d. 20 µm (New Objective) by stainless steel union, with a PEEK sleeve for coupling the nanospray with the on-line nano-LC. The voltage applied to the union in order to produce an electrospray was 2.4 kV. Helium was introduced as a collision gas at a pressure of 3 psi. LTQ Orbitrap mass spectrometer was operated in the data-dependent mode with the resolution set to a value of 60,000. Up to the 7 most intense ions per scan were fragmented and analyzed in the linear trap. For the analysis of tryptic peptides, survey scans were recorded in the FT-mode followed by data-dependent collision-induced dissociation (CID) of the 7 most-intense ions in the linear ion trap (LTQ).

LC-MS/MS analysis of the tryptic peptides generated by in-solution digestion. ULC/MS grade solvents were used for all chromatographic steps. Each sample was loaded using split-less nano-Ultra Performance Liquid Chromatography (10 kpsi nanoAcquity; Waters, Milford, Mass., USA). The buffers used were (A) H2O+0.1% formic acid and (B) ACN+0.1% formic acid. Desalting of samples was performed online using a reversed-phase C18 trapping column (180 mm id, 20 mm length, 5 mm particle size; Waters). The peptides were separated using a C18 T3 HSS nano-column (75 mm id, 150 mm length, 1.8 mm particle size; Waters) at 0.4 µL/min. Mobile phase consisted of A) H2O+0.1% formic acid and B) ACN+0.1% formic acid. The following gradient was used to elute the peptides: 3% to 30% B in 50 minutes, 30% to 95% B in 10 min, hold for 7 minutes and back to initial conditions. The nanoUPLC was coupled online through a nanoESI emitter (7 cm length, 10 mm tip; New Objective; Woburn, Mass., USA) to a quadrupole ion mobility time-of-flight (Q-IM-ToF) mass spectrometer (Synapt G2 HDMS, Waters) tuned to >20,000 mass resolution for both MS and MSMS (full width at half height). Data were acquired using Masslynx version 4.1 in MSE. In low-energy (MS) scans, the collision energy was set to 5 eV and this was ramped from 17 to 40 eV for high-energy scans (MS/MS). For both scans, the mass range was set to 50-1990 Da with a scan time set to 1 sec/scan. A reference compound (Glu-Fibrinopeptide B; Sigma) was infused continuously for external calibration using a LockSpray and scanned every 30 sec.

In-gel digested samples. The acquired spectra from Orbitrap-XL were submitted to in-house MASCOT server (version 2. 4, Matrix Science, London, UK (10)) and searched against a SwissProt and NCBI databases. Search parameters included fixed modification of 57.02146 Da (carboxyamidomethylation) on Cys, and variable modifications of 15.99491 Da (oxidation) on Met, 0.984016 Da (deamidation) on Asn and Gln (Q/N) and hydroxylation of Proline (Pro). The search parameters were as follows: maximum 2 missed cleavages, initial precursor ion mass tolerance 10 ppm, fragment ion mass tolerance 0.6 Da. Half-trypsin cleavage was allowed from ether end in order to detect collagenase cleaved peptides. The identity of the peptides were concluded from the detected collision-induced dissociation products by Mascot software and confirmed by manual inspection of the fragmentation series. Relative quantitation of the peptides revealing specific MMP1 and/or MMP13 cleavage sites was conducted with the Scaffold software (version Scaffold 3.6.3, Proteome Software Inc., Portland, Oreg., USA). To validate the datasets generated by MS, database search files generated by Mascot were imported into Scaffold and further analyzed from within Scaffold, using the spectral quantitative value display option with filter settings of: Min Protein 99%, Min #Peptides 2, min Peptide 95%. Each 21 Mascot outputs from searches of the 21 gel slices segments of each biological replicate were imported into Scaffold, combined and the number of assigned peptides and spectra in each biological replicates used for protein identification and quantification. The integrated PeptideProphet and ProteinProphet algorithms were used to control for false discovery rate and the probabilities were set to minimum 95% and 99%, respectively, and at least 2 unique matched peptides per protein were required for confident protein identification. To assign the cleavage sites of Col I to the MMPs digestion, the semi-tryptic peptides detected by MS were associated with the specificity of MMPs to collagen only (13). The cleavage sites from five experiments provided from silver and Comassie blue stains were analyzed. A list of proteolytic cleavage sites was divided for those reproducible in all experiments and those, which were randomly detected.

Analysis of the tryptic peptides generated by in-solution digestion. Raw data from mass spectrometer were imported into Rosetta Elucidators System, version 3.3 (Rosetta Biosoftware, Seattle, Wash., USA). Elucidator was used for alignment of raw MS1 data in RT and m/z dimensions as described. Aligned features were extracted and quantitative measurements obtained by integration of three-dimensional volumes (time, m/z, intensity) of each feature as detected in the MS1 scans. In parallel, database searching was carried out using Proteinlynx Global Server version 2.5 with the Ion Accounting algorithm described by Li et al. Data were searched against the rat Swiss-Prot database (version 2011_05), appended with the sequences of MMP1 and MMP13. Trypsin was set as the protease. One missed cleavage was allowed, and fixed modification was set to carbamidomethylation of cysteines. Variable modification included oxidation of methionine. The criteria for protein identification were set to minimum of three fragments per peptide, five fragments per protein, minimum peptide sequence of six amino acids and minimum of two peptides per protein. Data were also searched against the randomized version of each database and the maximum false identification rate was calculated to be less than 1% at a score cut-off of 6.5. This approach for setting the minimum identification score is based on reports by Keller and coworkers (termed Peptide Prophet). Additionally, we set the criteria such that peptides had to be detected in at least two out of three replicates and 67% of the samples in any one of the groups. Resulting peptide mixtures were compared based on peak intensities across all samples after retention time alignment and feature extraction. In all experiments a Student's T-Test was used to evaluate statistical significance of differential changes between the groups of MMP1, MMP13 and the control. P values were corrected for multiple hypotheses testing by Benjamin and Hochberg's Q value method. Significance threshold of Q value of ≤0.05 were considered for differences in Col I degradation by MMPs.

Rheological Characterization: The natural or degraded by MMP1 or MMP13 ECM were prepared and washed as described in paragraph 2 and then were laid tightly on the lower plate of rheometer, covering the entire surface of the plate. G', G" moduli were measured using Thermo Scientific rheometer in a plate-plate (P20 Ti L) configuration using HAAKE MARS at 25±0.1° C. (working gap of 0.3±0.05 mm) Dynamic frequency sweep analysis was conducted to measure the frequency-dependent storage (G') and loss (G") moduli of various ECMs in the range of 1-100 Hz. The excess of water from intact or degraded ECMs was delicately removed using KimWipe wipers.

Example 9: Screening Methods According to Some Embodiments of the Present Invention Screening Methods Utilizing Enzymatically Remodeled Uteri Uteri are extracted from female ICR mice (10 weeks old) that are mated with male ICR mice, according to the following method: On day 4 post coitum (E4.0) female mice are sacrificed (according to issued IACUC approval) and the uteri are extracted, washed in PBS buffer and flash frozen in liquid nitrogen. Uteri are de-cellurized by repeatedly freeze/thaw cycles following washing with 0.5% Na-dehydrocholate then extensive washing with DDW.

Test compounds or enzymes are then introduced to the de-cellularized uteri for 2 hours at 30/37 C then washed with DDW.

The ability of the test compound or enzyme to increase embryo implantation is assayed by examining the ability of the enzymatically-remodeled uteri to affect cell adherence, using adherent mammalian cells, such as, for example Rat1 cells. $7.5\times10^5$ cells are incubated with each remodeled uteri for 4 hours. The cells are then be lysed with RIPA buffer (137 mM NaCl, 20 mM Tris pH 7.4, 10% (v/v) glycerol, 1% Triton X-100, 0.5% (v/v) deoxycholate, 0.1% (w/v) SDS, 2 mM EDTA, 1 mM PMSF, 20 mM leupeptin). Using western blot analysis, the amount of adhered cells to remodeled uteri can be compared to controls, to identify the test compounds or enzymes that increase the rate of adherence of the cells to uteri.

The test compounds or enzymes identified in the cellular adhesion assay outlined above are then tested again by examining the ability of the enzymatically-remodeled uteri to affect the adhesion of murine oocytes, or murine embryos. 10 oocytes or 10 embryos are incubated with each remodeled uteri for 4 hours. The oocytes or embryos are then be lysed with RIPA buffer (137 mM NaCl, 20 mM Tris pH 7.4, 10% (v/v) glycerol, 1% Triton X-100, 0.5% (v/v) deoxycholate, 0.1% (w/v) SDS, 2 mM EDTA, 1 mM PMSF, 20 mM leupeptin). Using western blot analysis, the amount of adhered oocytes or embryos to remodeled uteri can be compared to controls, to identify the test compounds or enzymes that increase the rate of adherence of the oocytes or embryos to uteri.

The test compounds identified in the oocyte and embryo adhesion assays outlined above are then tested again by examining the ability of the compounds or enzymes to increase the implantation of embryos in uteri treated with the test compounds of enzymes, via IVF, or by natural conception.

Screening Methods Utilizing Enzymatically Remodeled ECM Fascicles

ECM fascicles, comprising Col I can be obtained using the methods described in Example 1. Test compounds or enzymes are then incubated with for 2 hours at 30/37 C then washed with DDW.

Figure 22B:
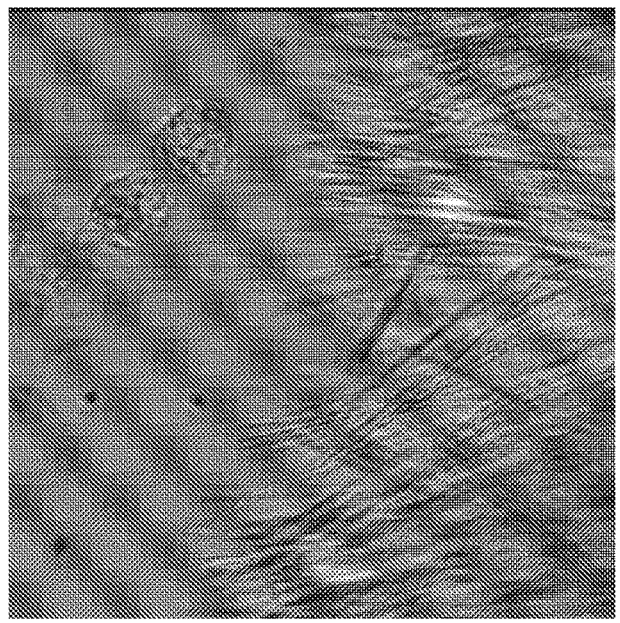
FIGS. 22A-22B show the effect of ECM remodeling on cell migration and cellular morphology.
Figure 22A:
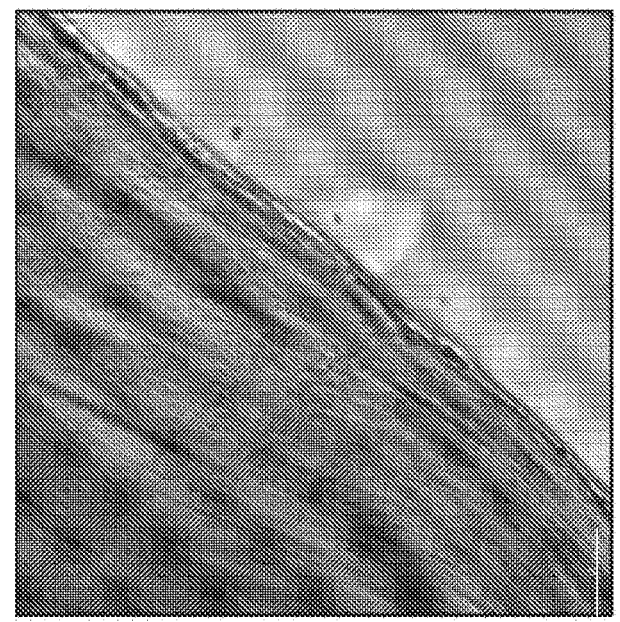

The ability of the test compound or enzyme to increase embryo implantation is assayed by examining the ability of the test compounds or enzymes to alter cellular morphology or adherence to the ECM fascicles. Referring to FIG. 22, treatment of ECM fascicles with MMP-1 influences cellular morphology, see FIG. 22B, compared to non-treated ECM fascicles (FIG. 22A). The ability of test compounds or enzymes to increase embryo implantation is assayed by examining the ability of the test compounds or enzymes to alter cellular morphology or adherence to the ECM fascicles, by comparing the appearance of cells adhered to treated ECM fascicles, to cells adhered to MMP-1 treated fascicles. The number of cells adhered to the collagen fibrils within the treated ECM fascicles may also be used to determine the ability of the test compound or enzyme to increase embryo implantation.

The test compounds or enzymes identified in the ECM fascicles assay outlined above are then tested again by examining the ability of the enzymatically-remodeled uteri to affect the adhesion of adherent cells, murine oocytes, or murine embryos to decellularized uteri. 10 oocytes or 10 embryos are incubated with each remodeled uteri for 4 hours. The cells oocytes or embryos are then be lysed with RIPA buffer (137 mM NaCl, 20 mM Tris pH 7.4, 10% (v/v) glycerol, 1% Triton X-100, 0.5% (v/v) deoxycholate, 0.1% (w/v) SDS, 2 mM EDTA, 1 mM PMSF, 20 mM leupeptin). Using western blot analysis, the amount of adhered oocytes or embryos to remodeled uteri can be compared to controls, to identify the test compounds or enzymes that increase the rate of adherence of the oocytes or embryos to uteri.

The test compounds identified in the cell, oocyte and embryo adhesion assays outlined above are then tested again by examining the ability of the compounds or enzymes to increase the implantation of embyros in uteri treated with the test compounds of enzymes, via IVF, or by natural conception.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the Applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of uterine preparation for insemination, the method comprising: administering to a mammal in an intrauterine manner at least one extra cellular matrix (ECM) remodeling enzyme selected from the group consisting of matrix metalloproteinase (MMP)-1 and MMP-13.

2. The method of claim 1, wherein the ECM remodeling enzyme is MMP-1.

3. The method of claim 1, wherein the mammal comprises a healthy uterus.

4. The method of claim 1, wherein said administering in an intrauterine manner is done with an intrauterine catheter.

5. The method of claim 1, wherein said mammal is a human.

6. The method of claim 1, wherein said mammal is a cow.

7. The method of claim 1, wherein said mammal is a dog.

8. The method of claim 1, wherein said mammal is a rodent.

9. The method of claim 1, wherein said remodeling enzyme is comprised in a pharmaceutical composition.

10. The method of claim 1, wherein said remodeling enzyme is in a pharmaceutical composition selected from the group consisting of a foam, a gel, a sponge, a capsule and a matrix.

11. The method of claim 1 further comprises inseminating the mammal.

12. The method of claim 11, wherein said inseminating is following said administering.

* * * * *